(12) United States Patent
Miller et al.

(10) Patent No.: US 10,363,136 B2
(45) Date of Patent: Jul. 30, 2019

(54) IMPLANT HAVING MULTIPLE ADJUSTMENT MECHANISMS

(71) Applicant: Valtech Cardio, Ltd., Or Yehuda (IL)

(72) Inventors: Eran Miller, Moshav Beit Elazari (IL); Tal Reich, Moledet (IL); Amir Gross, Tel Aviv-Jaffa (IL); Tal Sheps, Givat Shmuel (IL); Oz Cabiri, Hod Hasharon (IL)

(73) Assignee: Valtech Cardio, Ltd., Or Yehuda (IL)

( * ) Notice: Subject to any disclaimer, the term of this patent is extended or adjusted under 35 U.S.C. 154(b) by 0 days.

(21) Appl. No.: 15/717,440

(22) Filed: Sep. 27, 2017

(65) Prior Publication Data

US 2018/0014934 A1 Jan. 18, 2018

Related U.S. Application Data

(63) Continuation of application No. 14/990,172, filed on Jan. 7, 2016, now Pat. No. 9,775,709, which is a
(Continued)

(51) Int. Cl.
*A61F 2/24* (2006.01)

(52) U.S. Cl.
CPC .......... *A61F 2/2445* (2013.01); *A61F 2/2448* (2013.01); *A61F 2/2466* (2013.01);
(Continued)

(58) Field of Classification Search
CPC ........ A61F 2/24; A61F 2/2445; A61F 2/2448; A61F 2/2466; A61F 2/2487;
(Continued)

(56) References Cited

U.S. PATENT DOCUMENTS

| 3,604,488 A | 9/1971 | Wishart et al. |
| 3,656,185 A | 4/1972 | Carpentier |

(Continued)

FOREIGN PATENT DOCUMENTS

| EP | 1034753 A1 | 9/2000 |
| WO | 9205093 A1 | 4/1992 |

(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — Alvin J Stewart
(74) *Attorney, Agent, or Firm* — Thomas Richardson; Paul Kaye; Sanford T. Colb & Co.

(57) ABSTRACT

A method is provided for use with an implant structure, a first tool, a second tool, and a longitudinal guide member. The implant structure is delivered to a heart of a subject, the implant structure including: (i) a first adjustment mechanism to which the first tool is coupled, and (ii) a second adjustment mechanism to which the longitudinal guide member is coupled. The implant structure is then coupled to tissue of the heart. Subsequently, the second tool is advanced along the longitudinal guide member to the second adjustment mechanism.

22 Claims, 11 Drawing Sheets

Related U.S. Application Data continuation of application No. 14/486,226, filed on Sep. 15, 2014, now Pat. No. 9,265,608, which is a continuation of application No. 13/666,262, filed on Nov. 1, 2012, now Pat. No. 8,858,623.

(60) Provisional application No. 61/555,570, filed on Nov. 4, 2011.

(52) U.S. Cl.
CPC ............ *A61F 2/2454* (2013.01); *A61F 2/2457* (2013.01); *A61F 2250/001* (2013.01)

(58) Field of Classification Search
CPC .................. A61F 2/2454; A61F 2/2457; A61F 2250/001; A61B 5/1076
See application file for complete search history.

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,306,296 A | 4/1994 | Wright et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,674,279 A | 10/1997 | Wright et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 6,001,127 A | 12/1999 | Schoon et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,530,952 B2 | 3/2003 | Vesely |
| 6,533,772 B1 | 3/2003 | Sheds et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |

(56) References Cited

U.S. PATENT DOCUMENTS

| | | | |
|---|---|---|---|
| 6,709,456 | B2 | 3/2004 | Langberg et al. |
| 6,711,444 | B2 | 3/2004 | Koblish |
| 6,718,985 | B2 | 4/2004 | Hlavka et al. |
| 6,719,786 | B2 | 4/2004 | Ryan et al. |
| 6,723,038 | B1 | 4/2004 | Schroeder et al. |
| 6,726,716 | B2 | 4/2004 | Marquez |
| 6,726,717 | B2 | 4/2004 | Alfieri et al. |
| 6,730,121 | B2 | 5/2004 | Ortiz et al. |
| 6,749,630 | B2 | 6/2004 | McCarthy et al. |
| 6,752,813 | B2 | 6/2004 | Goldfarb et al. |
| 6,764,310 | B1 | 7/2004 | Ichihashi et al. |
| 6,764,510 | B2 | 7/2004 | Vidlund et al. |
| 6,764,810 | B2 | 7/2004 | Ma et al. |
| 6,770,083 | B2 | 8/2004 | Seguin |
| 6,786,924 | B2 | 9/2004 | Ryan et al. |
| 6,786,925 | B1 | 9/2004 | Schoon et al. |
| 6,790,231 | B2 | 9/2004 | Liddicoat et al. |
| 6,797,001 | B2 | 9/2004 | Mathis et al. |
| 6,797,002 | B2 | 9/2004 | Spence et al. |
| 6,802,319 | B2 | 10/2004 | Stevens et al. |
| 6,805,710 | B2 | 10/2004 | Bolling et al. |
| 6,805,711 | B2 | 10/2004 | Quijano et al. |
| 6,855,126 | B2 | 2/2005 | Flinchbaugh |
| 6,858,039 | B2 | 2/2005 | McCarthy |
| 6,884,250 | B2 | 4/2005 | Monassevitch et al. |
| 6,893,459 | B1 | 5/2005 | Macoviak |
| 6,908,478 | B2 | 6/2005 | Alferness et al. |
| 6,908,482 | B2 | 6/2005 | McCarthy et al. |
| 6,918,917 | B1 | 7/2005 | Nguyen et al. |
| 6,926,730 | B1 | 8/2005 | Nguyen et al. |
| 6,960,217 | B2 | 11/2005 | Bolduc |
| 6,964,684 | B2 | 11/2005 | Ortiz et al. |
| 6,964,686 | B2 | 11/2005 | Gordon |
| 6,976,995 | B2 | 12/2005 | Mathis et al. |
| 6,986,775 | B2 | 1/2006 | Morales et al. |
| 6,989,028 | B2 | 1/2006 | Lashinski et al. |
| 6,997,951 | B2 | 2/2006 | Solem et al. |
| 7,004,176 | B2 | 2/2006 | Lau |
| 7,007,798 | B2 | 3/2006 | Happonen et al. |
| 7,011,669 | B2 | 3/2006 | Kimblad |
| 7,011,682 | B2 | 3/2006 | Lashinski et al. |
| 7,018,406 | B2 | 3/2006 | Seguin et al. |
| 7,037,334 | B1 | 5/2006 | Hlavka et al. |
| 7,077,850 | B2 | 7/2006 | Kortenbach |
| 7,077,862 | B2 | 7/2006 | Vidlund et al. |
| 7,087,064 | B1 | 8/2006 | Hyde |
| 7,101,395 | B2 | 9/2006 | Tremulis et al. |
| 7,101,396 | B2 | 9/2006 | Artof et al. |
| 7,112,207 | B2 | 9/2006 | Allen et al. |
| 7,118,595 | B2 | 10/2006 | Ryan et al. |
| 7,125,421 | B2 | 10/2006 | Tremulis et al. |
| 7,150,737 | B2 | 12/2006 | Purdy et al. |
| 7,159,593 | B2 | 1/2007 | McCarthy et al. |
| 7,166,127 | B2 | 1/2007 | Spence et al. |
| 7,169,187 | B2 | 1/2007 | Datta et al. |
| 7,172,625 | B2 | 2/2007 | Shu et al. |
| 7,175,660 | B2 | 2/2007 | Cartledge et al. |
| 7,186,262 | B2 | 3/2007 | Saadat |
| 7,186,264 | B2 | 3/2007 | Liddicoat et al. |
| 7,189,199 | B2 | 3/2007 | McCarthy et al. |
| 7,192,443 | B2 | 3/2007 | Solem et al. |
| 7,220,277 | B2 | 5/2007 | Arru et al. |
| 7,226,467 | B2 | 6/2007 | Lucatero et al. |
| 7,226,477 | B2 | 6/2007 | Cox |
| 7,226,647 | B2 | 6/2007 | Kasperchik et al. |
| 7,229,452 | B2 | 6/2007 | Kayan |
| 7,238,191 | B2 | 7/2007 | Bachmann |
| 7,288,097 | B2 | 10/2007 | Seguin |
| 7,294,148 | B2 | 11/2007 | McCarthy |
| 7,297,150 | B2 | 11/2007 | Cartledge et al. |
| 7,311,728 | B2 | 12/2007 | Solem et al. |
| 7,311,729 | B2 | 12/2007 | Mathis et al. |
| 7,314,485 | B2 | 1/2008 | Mathis |
| 7,316,710 | B1 | 1/2008 | Cheng et al. |
| 7,329,279 | B2 | 2/2008 | Haug et al. |
| 7,329,280 | B2 | 2/2008 | Bolling et al. |
| 7,335,213 | B1 | 2/2008 | Hyde et al. |
| 7,361,190 | B2 | 4/2008 | Shaoulian et al. |
| 7,364,588 | B2 | 4/2008 | Mathis et al. |
| 7,377,941 | B2 | 5/2008 | Rhee et al. |
| 7,390,329 | B2 | 6/2008 | Westra et al. |
| 7,404,824 | B1 | 7/2008 | Webler et al. |
| 7,431,692 | B2 | 10/2008 | Zollinger et al. |
| 7,442,207 | B2 | 10/2008 | Rafiee |
| 7,452,376 | B2 | 11/2008 | Lim et al. |
| 7,455,690 | B2 | 11/2008 | Cartledge et al. |
| 7,485,142 | B2 | 2/2009 | Milo |
| 7,485,143 | B2 | 2/2009 | Webler et al. |
| 7,500,989 | B2 | 3/2009 | Solem et al. |
| 7,507,252 | B2 | 3/2009 | Lashinski et al. |
| 7,510,575 | B2 | 3/2009 | Spenser et al. |
| 7,510,577 | B2 | 3/2009 | Moaddeb et al. |
| 7,527,647 | B2 | 5/2009 | Spence |
| 7,530,995 | B2 | 5/2009 | Quijano et al. |
| 7,549,983 | B2 | 6/2009 | Roue et al. |
| 7,559,936 | B2 | 7/2009 | Levine |
| 7,562,660 | B2 | 7/2009 | Saadat |
| 7,563,267 | B2 | 7/2009 | Goldfarb et al. |
| 7,563,273 | B2 | 7/2009 | Goldfarb et al. |
| 7,569,062 | B1 | 8/2009 | Kuehn et al. |
| 7,585,321 | B2 | 9/2009 | Cribier |
| 7,588,582 | B2 | 9/2009 | Starksen et al. |
| 7,591,826 | B2 | 9/2009 | Alferness et al. |
| 7,604,646 | B2 | 10/2009 | Goldfarb et al. |
| 7,608,091 | B2 | 10/2009 | Goldfarb et al. |
| 7,608,103 | B2 | 10/2009 | McCarthy |
| 7,625,403 | B2 | 12/2009 | Krivoruchko |
| 7,632,303 | B1 | 12/2009 | Stalker et al. |
| 7,635,329 | B2 | 12/2009 | Goldfarb et al. |
| 7,635,386 | B1 | 12/2009 | Gammie |
| 7,655,015 | B2 | 2/2010 | Goldfarb et al. |
| 7,666,204 | B2 | 2/2010 | Thornton et al. |
| 7,682,319 | B2 | 3/2010 | Martin et al. |
| 7,682,369 | B2 | 3/2010 | Seguin |
| 7,686,822 | B2 | 3/2010 | Shayani |
| 7,699,892 | B2 | 4/2010 | Rafiee et al. |
| 7,704,269 | B2 | 4/2010 | St. Goar et al. |
| 7,704,277 | B2 | 4/2010 | Zakay et al. |
| 7,722,666 | B2 | 5/2010 | Lafontaine |
| 7,736,388 | B2 | 6/2010 | Goldfarb et al. |
| 7,748,389 | B2 | 7/2010 | Salahieh et al. |
| 7,753,924 | B2 | 7/2010 | Starksen et al. |
| 7,758,632 | B2 | 7/2010 | Hojeibane et al. |
| 7,780,726 | B2 | 8/2010 | Seguin |
| 7,871,368 | B2 | 1/2011 | Zollinger et al. |
| 7,871,433 | B2 | 1/2011 | Lattouf |
| 7,883,475 | B2 | 2/2011 | Dupont et al. |
| 7,883,538 | B2 | 2/2011 | To et al. |
| 7,892,281 | B2 | 2/2011 | Seguin et al. |
| 7,927,370 | B2 | 4/2011 | Webler et al. |
| 7,927,371 | B2 | 4/2011 | Navia et al. |
| 7,942,927 | B2 | 5/2011 | Kaye et al. |
| 7,947,056 | B2 | 5/2011 | Griego et al. |
| 7,955,315 | B2 | 6/2011 | Feinberg et al. |
| 7,955,377 | B2 | 6/2011 | Melsheimer |
| 7,992,567 | B2 | 8/2011 | Hirotsuka et al. |
| 7,993,368 | B2 | 8/2011 | Gambale et al. |
| 7,993,397 | B2 | 8/2011 | Lashinski et al. |
| 8,012,201 | B2 | 9/2011 | Lashinski et al. |
| 8,034,103 | B2 | 10/2011 | Burriesci et al. |
| 8,052,592 | B2 | 11/2011 | Goldfarb et al. |
| 8,057,493 | B2 | 11/2011 | Goldfarb et al. |
| 8,062,355 | B2 | 11/2011 | Figulla et al. |
| 8,070,804 | B2 | 12/2011 | Hyde et al. |
| 8,070,805 | B2 | 12/2011 | Vidlund et al. |
| 8,075,616 | B2 | 12/2011 | Solem et al. |
| 8,100,964 | B2 | 1/2012 | Spence |
| 8,123,801 | B2 | 2/2012 | Milo |
| 8,142,493 | B2 | 3/2012 | Spence et al. |
| 8,142,495 | B2 | 3/2012 | Hasenkam et al. |
| 8,142,496 | B2 | 3/2012 | Berreklouw |
| 8,147,542 | B2 | 4/2012 | Maisano et al. |
| 8,152,844 | B2 | 4/2012 | Rao et al. |
| 8,163,013 | B2 | 4/2012 | Machold et al. |

(56) References Cited

U.S. PATENT DOCUMENTS

| | | | |
|---|---|---|---|
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 * | 10/2014 | Miller .................. A61F 2/2445 623/2.36 |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,695 B2 * | 1/2015 | Gross .................. A61B 17/064 623/2.36 |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 * | 2/2016 | Miller .................. A61F 2/2445 |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,693,865 B2 | 7/2017 | Gilmore et al. |
| 9,730,793 B2 | 8/2017 | Reich et al. |
| 9,775,709 B2 * | 10/2017 | Miller .................. A61F 2/2445 |
| 9,788,941 B2 | 10/2017 | Hacohen |
| 9,801,720 B2 | 10/2017 | Gilmore et al. |
| 9,907,547 B2 | 3/2018 | Gilmore et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204195 A1 | 10/2003 | Keane et al. |
| 2003/0229350 A1 | 12/2003 | Kay |
| 2003/0229395 A1 | 12/2003 | Cox |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0059413 A1 | 3/2004 | Argento |
| 2004/0122514 A1 | 6/2004 | Fogarty et al. |
| 2004/0127982 A1 | 7/2004 | Machold et al. |
| 2004/0133274 A1 | 7/2004 | Webler et al. |

(56) References Cited

U.S. PATENT DOCUMENTS

| | | |
|---|---|---|
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260393 A1 | 12/2004 | Randert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0256532 A1* | 11/2005 | Nayak ............... A61B 17/0057 606/151 |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb |
| 2007/0162111 A1 | 7/2007 | Fukamachi et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091257 A1 | 4/2008 | Andreas et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |

(56) References Cited

U.S. PATENT DOCUMENTS

| | | |
|---|---|---|
| 2008/0281411 A1 | 11/2008 | Berreklouw |
| 2008/0288044 A1 | 11/2008 | Osborne |
| 2008/0288062 A1 | 11/2008 | Andrieu et al. |
| 2008/0300537 A1 | 12/2008 | Bowman |
| 2008/0300629 A1 | 12/2008 | Surti |
| 2009/0028670 A1 | 1/2009 | Garcia et al. |
| 2009/0043381 A1 | 2/2009 | Macoviak et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130992 A1 | 5/2010 | Machold et al. |
| 2010/0152845 A1 | 6/2010 | Bloom |
| 2010/0161043 A1 | 6/2010 | Maisano et al. |
| 2010/0161047 A1* | 6/2010 | Cabiri ............ A61F 2/2445 623/2.37 |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0106247 A1* | 5/2011 | Miller ............ A61B 17/0401 623/2.17 |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0224785 A1* | 9/2011 | Hacohen ............ A61B 17/0401 623/2.18 |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0022639 A1* | 1/2012 | Hacohen ............ A61B 17/068 623/2.11 |
| 2012/0022640 A1* | 1/2012 | Gross ................ A61B 17/068 623/2.11 |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0095552 A1 | 4/2012 | Spence et al. |
| 2012/0109155 A1 | 5/2012 | Robinson et al. |
| 2012/0136436 A1* | 5/2012 | Cabiri ............ A61F 2/2442 623/2.37 |
| 2012/0150290 A1 | 6/2012 | Gabbay |
| 2012/0158021 A1 | 6/2012 | Morrill |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0283757 A1* | 11/2012 | Miller ............ A61B 17/0401 606/151 |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1* | 2/2013 | Cartledge ............ A61F 2/95 623/1.11 |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0268069 A1 | 10/2013 | Zakai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2014/0088368 A1 | 3/2014 | Park |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0275757 A1 | 9/2014 | Goodwin et al. |

(56) References Cited

U.S. PATENT DOCUMENTS

| | | | |
|---|---|---|---|
| 2014/0276648 A1 | 9/2014 | Hammer et al. | |
| 2014/0296962 A1* | 10/2014 | Cartledge | A61F 2/243 623/1.12 |
| 2014/0303649 A1 | 10/2014 | Nguyen et al. | |
| 2014/0303720 A1 | 10/2014 | Sugimoto et al. | |
| 2014/0309661 A1 | 10/2014 | Sheps et al. | |
| 2014/0309730 A1 | 10/2014 | Alon et al. | |
| 2014/0343668 A1 | 11/2014 | Zipory et al. | |
| 2014/0350660 A1 | 11/2014 | Cocks et al. | |
| 2014/0379006 A1 | 12/2014 | Sutherland et al. | |
| 2015/0018940 A1 | 1/2015 | Quill et al. | |
| 2015/0051697 A1 | 2/2015 | Spence et al. | |
| 2015/0081014 A1 | 3/2015 | Gross et al. | |
| 2015/0112432 A1* | 4/2015 | Reich | A61F 2/2445 623/2.11 |
| 2015/0127097 A1 | 5/2015 | Neumann et al. | |
| 2015/0182336 A1 | 7/2015 | Zipory et al. | |
| 2015/0272586 A1 | 10/2015 | Herman et al. | |
| 2015/0272734 A1 | 10/2015 | Sheps et al. | |
| 2015/0282931 A1 | 10/2015 | Brunnett et al. | |
| 2016/0008132 A1 | 1/2016 | Cabin et al. | |
| 2016/0058557 A1 | 3/2016 | Reich et al. | |
| 2016/0113767 A1 | 4/2016 | Miller et al. | |
| 2016/0120645 A1* | 5/2016 | Alon | A61F 2/2442 623/2.4 |
| 2016/0158008 A1 | 6/2016 | Miller et al. | |
| 2016/0242762 A1 | 8/2016 | Gilmore et al. | |
| 2016/0262755 A1 | 9/2016 | Zipory et al. | |
| 2016/0302917 A1 | 10/2016 | Schewel | |
| 2016/0317302 A1 | 11/2016 | Madjarov et al. | |
| 2016/0361058 A1 | 12/2016 | Bolduc et al. | |
| 2016/0361168 A1* | 12/2016 | Gross | A61F 2/2445 |
| 2016/0361169 A1* | 12/2016 | Gross | A61F 2/2445 |
| 2017/0000609 A1* | 1/2017 | Gross | A61F 2/2445 |
| 2017/0245993 A1 | 8/2017 | Gross et al. | |
| 2018/0049875 A1 | 2/2018 | Iflah et al. | |

FOREIGN PATENT DOCUMENTS

| | | | |
|---|---|---|---|
| WO | 9846149 | A1 | 10/1998 |
| WO | 02085250 | A3 | 2/2003 |
| WO | 03047467 | A1 | 6/2003 |
| WO | 2010000454 | A1 | 1/2010 |
| WO | 2012176195 | A3 | 3/2013 |
| WO | 2014064964 | A1 | 5/2014 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al., "The edge to edge technique," The European Association for Cardio-Thoracic Surgery 14th Annual Meeting Oct. 7-11, Book of Procees. (2000).

Alfieri et al."Novel Suture Device for Beating-Heart Mitral Leaflet Approximation", Ann Thorac Surg. 2002, 74:1488-1493.

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

Amplatzer® Cribriform Occluder. A patient guide to Percutaneous, Transcatheter, Atrial Septal Defect Closuer, AGA Medical Corporation, Apr. 2008.

Amplatzer® Septal Occluder. A patient guide to the Non-Surgical Closuer of the Atrial Septal Defect Using the Amplatzer Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al."Experience with an adjustable pulmonary artery banding device in two cases: initial success-midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. Ring+String, Successful Repair technique for ischemic mitral regurgitation with severe leaflet Tethering, The Department of Thoracic Cardiovascular surgery, Hamburg, Germany, Nov. 2008.

Maisano, The double-orifice technique as a standardized approach to treat mitral . . . , European Journal of Cardio-thoracic Surgery 17 (2000) 201-205.

Odell JA et al., "Early Results o4yf a Simplified Method of Mitral Valve Annuloplasty," Circulation 92:150-154 (1995).

O'Reilly S et al., "Heart valve surgery pushes the envelope," Medtech Insight 8(3): 73, 99-108 (2006).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

* cited by examiner

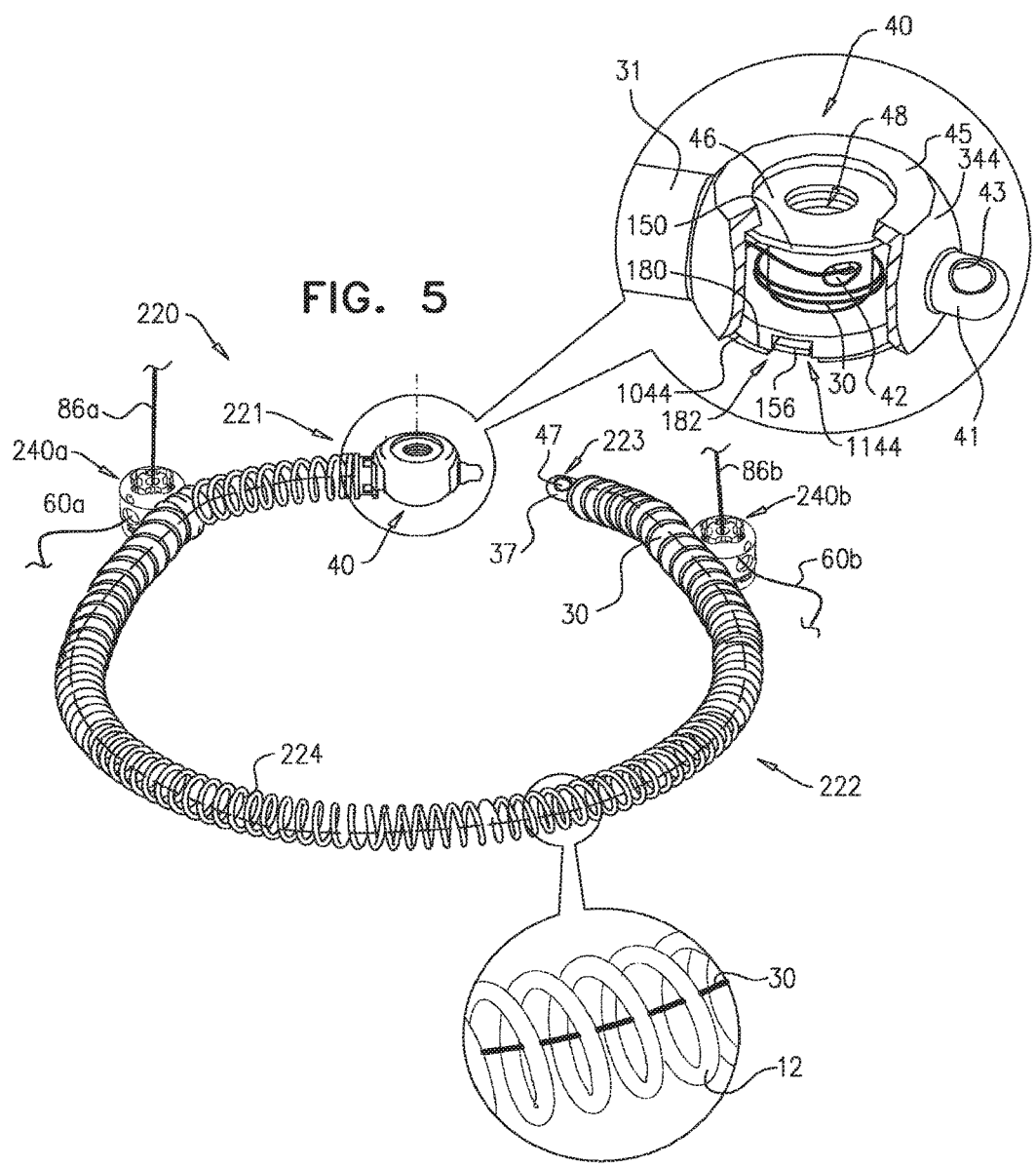

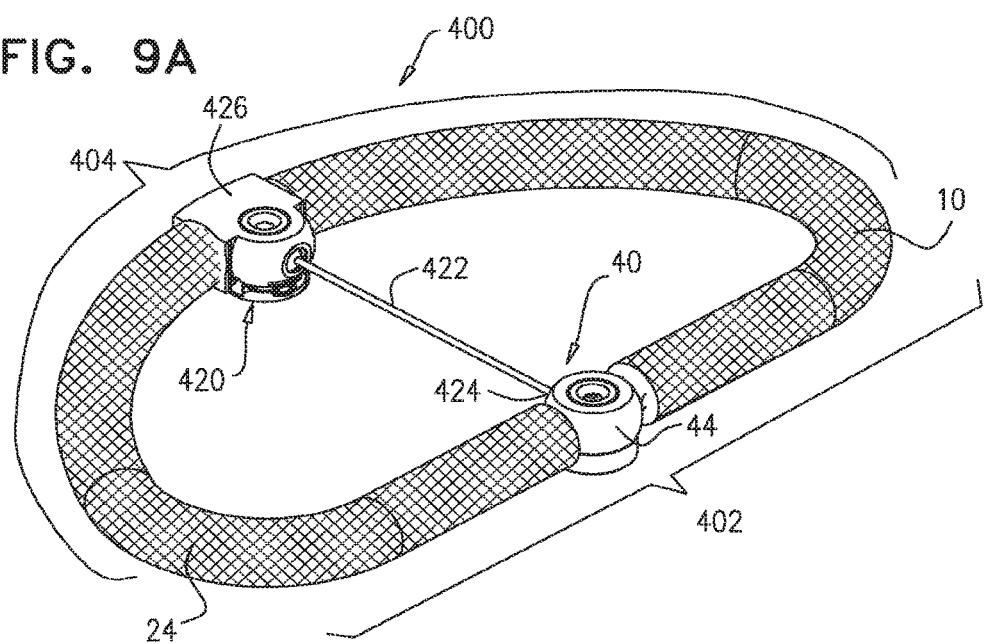
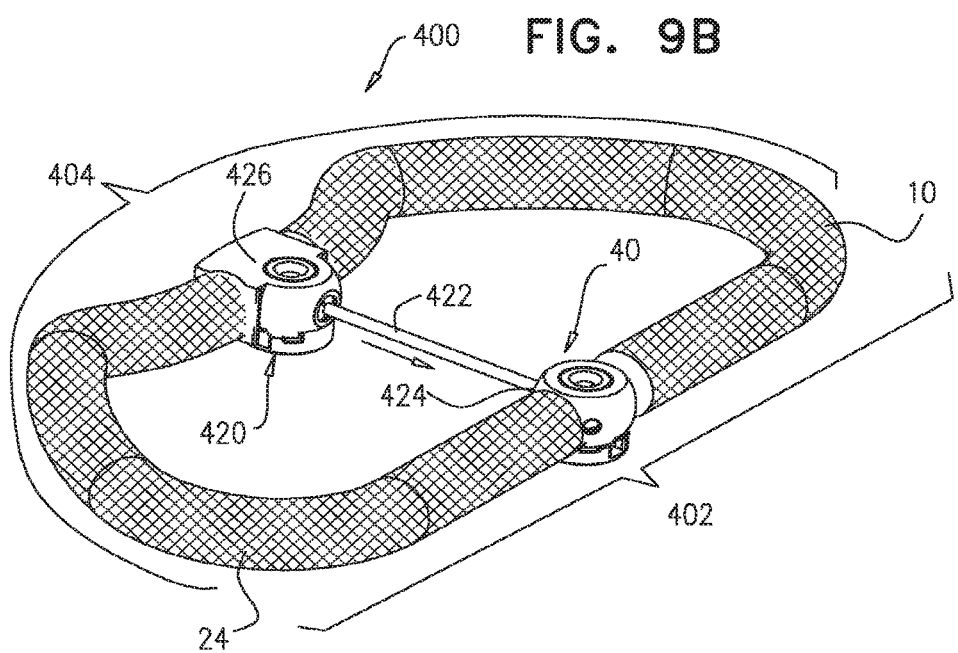

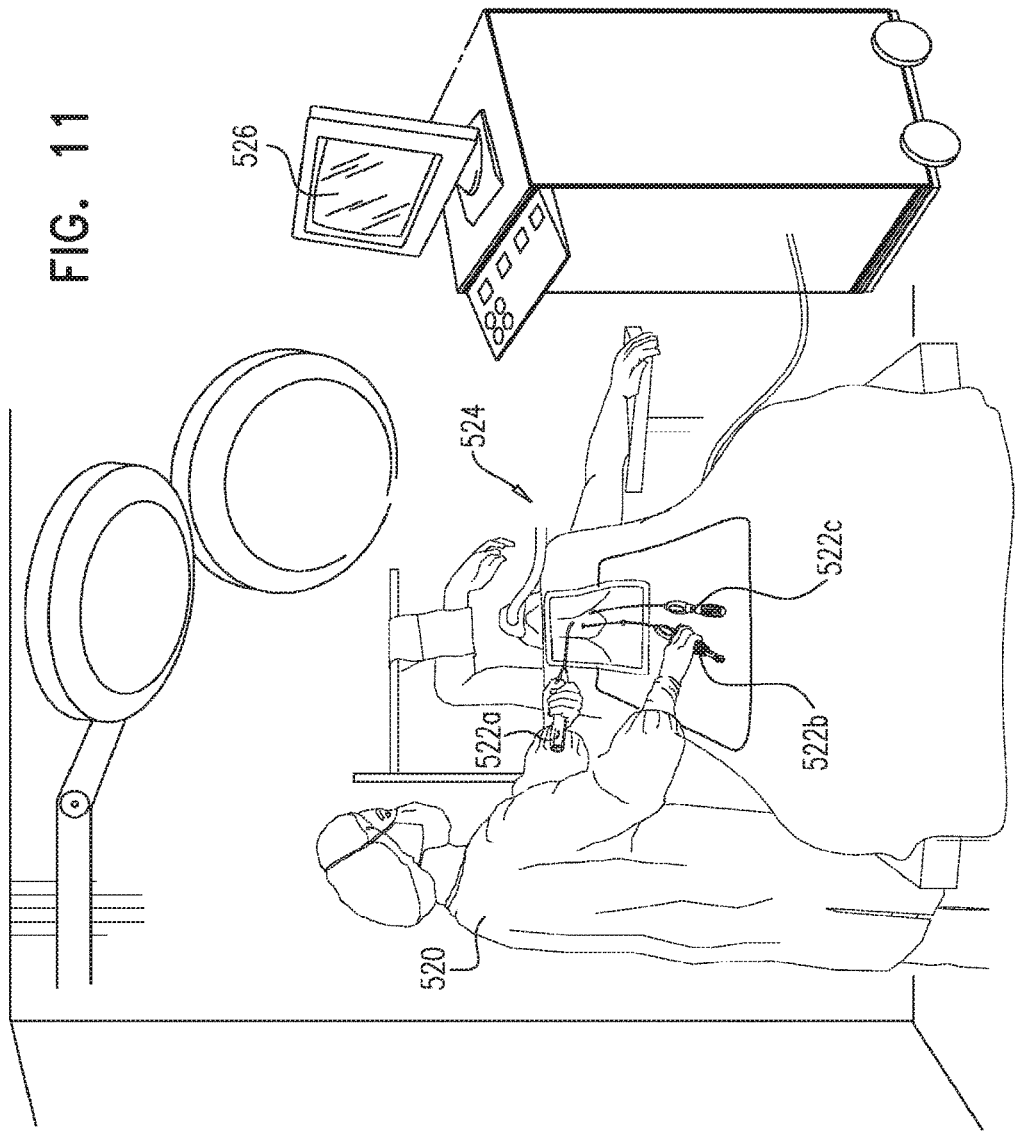

IMPLANT HAVING MULTIPLE ADJUSTMENT MECHANISMS

CROSS-REFERENCES TO RELATED APPLICATIONS

The present application is a Continuation of U.S. patent application Ser. No. 14/990,172 to Miller et al., filed Jan. 7, 2016, which published as US 2016/0113767 (now U.S. Pat. No. 9,775,709), and which is a Continuation of U.S. patent application Ser. No. 14/486,226 to Miller et al., filed Sep. 15, 2014, and entitled "Implant having multiple rotational assemblies," which published as US 2015/0012087 (now U.S. Pat. No. 9,265,608), and which is a Continuation of U.S. patent application Ser. No. 13/666,262 to Miller et al, filed Nov. 1, 2012, and entitled "Implant having multiple rotational assemblies", which published as US 2013/0116780 (now U.S. Pat. No. 8,858,623), and which claims priority from U.S. Provisional Application 61/555,570, filed on Nov. 4, 2011, which are each incorporated herein by reference.

FIELD OF THE INVENTION

The present invention relates in general to valve repair. More specifically, the present invention relates to repair of a mitral valve of a patient.

BACKGROUND

Mitral regurgitation (MR), mitral insufficiency or mitral incompetence is a disorder of the heart in which the mitral valve does not close properly when the heart pumps out blood. It is the abnormal leaking of blood from the left ventricle, through the mitral valve, and into the left atrium, when the left ventricle contracts, i.e. there is regurgitation of blood back into the left atrium. MR is the most common form of valvular heart disease.

In functional mitral valve regurgitation (FMR), otherwise known as Secondary mitral regurgitation is characterized as the abnormal function of anatomically normal valve, i.e., the papillary muscles, chordae, and valve leaflets are otherwise normal. Regurgitation, the result of incomplete closure of normal leaflets occurs in a quarter of patients after myocardial infarction and up to 50% of those with heart failure.

FMR can be either due to ischemia and any cause of dilated left ventricle including, annular enlargement secondary to left ventricular dilatation, or papillary muscle displacement due to left ventricular remodeling, which results in tethering and excess tenting of the mitral valve leaflets.

Severe FMR is indicative of poor hemodynamics and typically a bad prognosis for the patient.

SUMMARY OF THE INVENTION

In some applications of the present invention, apparatus is provided comprising an implant structure comprising an adjustable annuloplasty ring structure coupled to at least first and second adjusting mechanisms, each comprising a respective rotatable structure. At least a portion of the annuloplasty ring structure comprises a flexible, longitudinally-compressible segment (e.g., coiled structures, stent-like struts, and/or a braided mesh). The annuloplasty structure is shaped to define a flexible, tubular body portion that is shaped so as to define a lumen thereof that houses at least one flexible longitudinal contracting member. The at least one flexible longitudinal contracting member is coupled to the first adjusting mechanism at a first portion of the flexible longitudinal contracting member. A second portion of the flexible longitudinal contracting member is coupled to a portion of the tubular body portion. The first adjusting mechanism is configured to adjust a perimeter of the annuloplasty ring structure by adjusting a degree of tension of the flexible member housed within the lumen of the annuloplasty structure. For example, the first adjusting mechanism is configured to contract the ring structure in response to rotation in a first rotational direction of the rotational structure of the first adjusting mechanism. The first adjusting mechanism is typically aligned with the tubular body portion.

Typically, the annuloplasty structure is configured to be implanted along a native annulus of an atrioventricular valve of a patient.

For some applications of the present invention, the second adjusting mechanism is coupled to an outer surface of the tubular body portion. The second adjusting mechanism is coupled to a first portion of a flexible longitudinal tension member. The flexible longitudinal tension member is configured to pass from the annuloplasty ring structure on the annulus of the valve of and into a ventricle. A second portion of the flexible longitudinal tension member is coupled to a tissue-engaging element configured to engage cardiac tissue in a vicinity of the ventricle (e.g., a portion of papillary muscle tissue, a portion of tissue of an inner wall of the ventricle, or a portion of tissue of an outer wall of the ventricle). For some applications, the tissue-engaging element comprises a sharp portion for penetrating the cardiac tissue. For some applications, the tissue-engaging element comprises a planar element abutting against tissue of the patient. Typically, the second portion of the flexible longitudinal tension member is configured to be coupled to a papillary muscle of the patient. The second adjusting mechanism is configured to adjust a degree of tension of the flexible longitudinal tension member in a manner sufficient to (a) adjust a position of the papillary muscle, (b) adjust a degree of distension of the ventricular wall, and/or (c) have the flexible longitudinal tension member function as an artificial chordae tendineae. For applications in which the position of the papillary muscle is adjusted such positioning typically provides therapy to the patient.

For some applications of the present invention, an annuloplasty ring structure comprises two or more adjusting mechanisms configured to shape the annuloplasty ring structure into a desired shape. For example, the two or more adjusting mechanisms function, upon actuation thereof, to form the adjustable ring into a saddle shape. Alternatively or additionally, the two or more adjusting mechanisms function, upon actuation thereof, to draw together opposing portions of the ring.

Typically, the annuloplasty ring structures described herein, the adjusting mechanisms, and the flexible longitudinal members are advanced and implanted in an open-heart procedure. For some applications, devices described herein may be implanted using a minimally-invasive or percutaneous transcatheter procedure.

Methods for delivery and use of the invention are also described.

There is therefore provided, in accordance with an application of the present invention, apparatus for use with a native valve of a heart of a patient, the native valve having a valve annulus, and the heart having a ventricle, the apparatus including:

an annuloplasty structure, shaped to define a perimeter, and configured to be disposed at the annulus of the native valve of the patient;

a first adjusting mechanism, coupled to the annuloplasty structure, and configured to adjust the perimeter of the annuloplasty structure;

at least one longitudinal flexible member, having a first end portion, and a second end portion that is configured to be coupled to tissue of the ventricle of the heart of the patient; and at least a second adjusting mechanism:
coupled to the annuloplasty structure such that the second adjusting mechanism is slidable around at least part of the perimeter of the annuloplasty structure,
coupled to the first end portion of the at least one longitudinal flexible member, and
configured to adjust a distance between the second adjusting mechanism and the second end portion of the at least one longitudinal flexible member.

In an application:
the annuloplasty structure is configured to be implanted at an annulus of a mitral valve of the patient,
the at least second adjusting mechanism is configured to be coupled to a location along the annulus, in a vicinity of a fibrous trigone adjacent to the mitral valve.

In an application, the apparatus further includes a plurality of sutures, each suture of the plurality of sutures being configured to be fastened to a respective location along a circumference of an annulus of a mitral valve of the patient, the plurality of sutures being configured to facilitate advancement of the annuloplasty structure toward the annulus.

In an application, the annuloplasty structure includes a coiled structure having a lumen.

In an application, the annuloplasty structure includes a partial annuloplasty ring.

In an application, the annuloplasty structure includes a full annuloplasty ring.

In an application, the annuloplasty structure is coated with polytetrafluoroethylene.

In an application, the annuloplasty structure has a first end and a second end, and a longitudinal axis therebetween, and the second adjusting mechanism is movable along the longitudinal axis of the annuloplasty structure.

In an application, the annuloplasty structure includes a body portion that defines a lumen therethrough, and the annuloplasty structure further includes a flexible longitudinal contracting member, having a first end portion, a second end portion, and a middle portion between the first and second end portions, at least one of the end portions being coupled to the first adjusting mechanism, and the middle portion being disposed within the lumen of the body portion.

In an application, the first adjusting mechanism is configured to reversibly adjust the perimeter of the annuloplasty structure, and the second adjusting mechanism is configured to reversibly adjust the distance.

In an application, the second adjusting mechanism is configured to adjust the distance between the second adjusting mechanism and the second end portion of the at least one longitudinal flexible member, independently of the adjusting of the perimeter of the annuloplasty structure by the first adjusting mechanism.

In an application:
the at least one longitudinal flexible member includes a first longitudinal flexible member and a second longitudinal flexible member, the first and second longitudinal members each having a first end portion and a second end portion, the second portion of the first longitudinal flexible member being configured to be coupled to a first portion of the tissue, and the second portion of the second longitudinal flexible member being configured to be coupled to a second portion of the tissue, the second adjusting mechanism is coupled to the first end portion of the first longitudinal flexible member, and is configured to adjust a distance between the second adjusting mechanism and the second end portion of the first longitudinal flexible member, the apparatus further includes a third adjusting mechanism, coupled to the annuloplasty structure and to the first end portion of the second longitudinal flexible member, and is configured to adjust a distance between the third adjusting mechanism and the second end portion of the second longitudinal flexible member.

In an application:
at least one selected from the group consisting of the first portion of the tissue and the second portion of the tissue, includes tissue of a papillary muscle of the patient, and at least one selected from the group consisting of the second adjusting mechanism and the third adjusting mechanism, is configured to adjust a distance between the papillary muscle and the annuloplasty structure.

In an application, the third adjusting mechanism is configured to adjust the distance between the third adjusting mechanism and the second end portion of the second longitudinal flexible member, independently of the adjustment, by the second adjusting mechanism, of the distance between the second adjusting mechanism and the second end portion of the first longitudinal flexible member.

In an application, the first adjusting mechanism includes a first rotatable adjusting mechanism, and the second adjusting mechanism includes a second rotatable adjusting mechanism.

In an application, the first rotatable adjusting mechanism and the second rotatable adjusting mechanism are both rotatable bidirectionally.

In an application, the second rotatable adjusting mechanism includes a spool, and the spool is configured to pull the tissue toward the annuloplasty structure, via the longitudinal flexible member, responsively to rotation of the spool.

In an application, the apparatus further includes a rotation tool, configured to rotate the first rotatable adjusting mechanism.

In an application, the rotation tool includes an elongate rotation tool, configured to extend from outside the patient, to the first rotatable adjusting mechanism.

In an application, the rotation tool is configured to facilitate adjustment of the first adjusting mechanism while the heart of the patient is beating.

In an application, the rotation tool includes a first rotation tool, and the apparatus further includes a second rotation tool, configured to rotate the second rotatable adjusting mechanism.

In an application, at least the first adjusting mechanism includes a locking mechanism:
having an unlocked state in which the first adjusting mechanism is adjustable, having
having a locked state in which the locking mechanism inhibits adjustment of the first adjusting mechanism, and
configured to be intracorporeally moved from the locked state to the unlocked state.

In an application, the first rotation tool is configured to intracorporeally move the first rotatable adjusting mechanism into the unlocked configuration thereof.

In an application, the tissue includes papillary muscle tissue of the patient, and apparatus is configured to relocate the papillary muscle tissue, by pulling the papillary muscle tissue toward the annuloplasty structure.

In an application:
the annuloplasty structure is configured to be implanted at an annulus of a mitral valve of the patient, and
the longitudinal flexible member is configured to relocate the papillary muscle tissue, in response to the pulling by the adjusting mechanism.

In an application, the longitudinal flexible member is configured to perform a therapy by relocating the patient's papillary muscle tissue.

In an application, the annuloplasty structure is configured to be implanted at an annulus of a mitral valve of the patient, and the apparatus is configured to be transcatheterally advanced toward the annulus.

In an application, the apparatus is configured to be transluminally advanced toward the annulus.

In an application, the second end portion of the longitudinal flexible member includes a tissue-coupling element.

In an application, the tissue-coupling element includes an anchor having at least one sharp portion.

There is further provided, in accordance with an application of the present invention, apparatus for use with a native valve of a heart of a patient, the native valve having a valve annulus, and the heart having a ventricle, the apparatus including:

an annuloplasty structure, shaped to define a perimeter, and configured to be disposed at the annulus of the native valve of the patient;

a first adjusting mechanism, coupled to the annuloplasty structure, and configured to reversibly adjust the perimeter of the annuloplasty structure;

at least one longitudinal flexible member, having a first end portion, and a second end portion that is configured to be coupled to tissue of the ventricle of the heart of the patient; and at least a second adjusting mechanism, coupled to the annuloplasty structure and to the first end portion of the at least one longitudinal flexible member, and configured to reversibly adjust a distance between the second adjusting mechanism and the second end portion of the at least one longitudinal flexible member.

In an application, the annuloplasty structure has a first end and a second end, and a longitudinal axis therebetween, and the second adjusting mechanism is movable along the longitudinal axis of the annuloplasty structure.

In an application, the annuloplasty structure includes a body portion that defines a lumen therethrough, and the annuloplasty, structure further includes a flexible longitudinal contracting member, having a first end portion, a second end portion, and a middle portion between the first and second end portions, at least one of the end portions being coupled to the first adjusting mechanism, and the middle portion being disposed within the lumen of the body portion.

In an application, the first adjusting mechanism is movably coupled to the annuloplasty structure.

In an application, the annuloplasty structure includes a partial annuloplasty ring.

In an application, the annuloplasty structure includes a full annuloplasty ring.

In an application, the annuloplasty structure is coated with polytetrafluoroethylene.

In an application:
the annuloplasty structure is configured to be implanted at an annulus of a mitral valve of the patient,
the at least second adjusting mechanism is configured to be coupled to a location along the annulus, in a vicinity of a fibrous trigone adjacent to the mitral valve.

In an application, the apparatus further includes a plurality of sutures, each suture of the plurality of sutures being configured to be fastened to a respective location along a circumference of an annulus of a mitral valve of the patient, the plurality of sutures being configured to facilitate advancement of the annuloplasty structure toward the annulus.

In an application, the annuloplasty structure includes a coiled structure having a lumen.

In an application, the second adjusting mechanism is configured to reversibly adjust the distance between the second adjusting mechanism and the second end portion of the at least one longitudinal flexible member, independently of the reversible adjusting of the perimeter of the annuloplasty structure by the first adjusting mechanism.

In an application:
the at least one longitudinal flexible member includes a first longitudinal flexible member and a second longitudinal flexible member, the first and second longitudinal members each having a first end portion and a second end portion, the second portion of the first longitudinal flexible member being configured to be coupled to a first portion of the tissue, and the second portion of the second longitudinal flexible member being configured to be coupled to a second portion of the tissue, the second adjusting mechanism is coupled to the first end portion of the first longitudinal flexible member, and is configured to reversibly adjust a distance between the second adjusting mechanism and the second end portion of the first longitudinal flexible member, the apparatus further includes a third adjusting mechanism, coupled to the annuloplasty structure and to the first end portion of the second longitudinal flexible member, and is configured to reversibly adjust a distance between the third adjusting mechanism and the second end portion of the second longitudinal flexible member.

In an application:
at least one selected from the group consisting of the first portion of the tissue and the second portion of the tissue, includes tissue of a papillary muscle of the patient, and
at least one selected from the group consisting of the second adjusting mechanism and the third adjusting mechanism, is configured to reversibly adjust a distance between the papillary muscle and the annuloplasty structure.

In an application, the third adjusting mechanism is configured to reversibly adjust the distance between the third adjusting mechanism and the second end portion of the second longitudinal flexible member, independently of the reversible adjustment, by the second adjusting mechanism, of the distance between the second adjusting mechanism and the second end portion of the first longitudinal flexible member.

In an application, the first adjusting mechanism includes a first rotatable adjusting mechanism, and the second adjusting mechanism includes a second rotatable adjusting mechanism.

In an application, the first rotatable adjusting mechanism and the second rotatable adjusting mechanism are both rotatable bidirectionally.

In an application, the second rotatable adjusting mechanism includes a spool, and the spool is configured to pull the tissue toward the annuloplasty structure, via the longitudinal flexible member, responsively to rotation of the spool.

In an application, the apparatus further includes a rotation tool, configured to rotate the first rotatable adjusting mechanism.

In an application, the rotation tool includes an elongate rotation tool, configured to extend from outside the patient, to the first rotatable adjusting mechanism.

In an application, the rotation tool is configured to facilitate reversible adjustment of the first adjusting mechanism while the heart of the patient is beating.

In an application, the rotation tool includes a first rotation tool, and the apparatus further includes a second rotation tool, configured to rotate the second rotatable adjusting mechanism.

In an application, at least the first adjusting mechanism includes a locking mechanism:

having an unlocked state in which the first adjusting mechanism is adjustable, having having a locked state in which the locking mechanism inhibits adjustment of the first adjusting mechanism, and configured to be intracorporeally moved from the locked state to the unlocked state.

In an application, the first rotation tool is configured to intracorporeally move the first rotatable adjusting mechanism into the unlocked configuration thereof.

In an application, the tissue includes papillary muscle tissue of the patient, and apparatus is configured to relocate the papillary muscle tissue, by pulling the papillary muscle tissue toward the annuloplasty structure.

In an application:

the annuloplasty structure is configured to be implanted at an annulus of a mitral valve of the patient, and the longitudinal flexible member is configured to relocate the papillary muscle tissue, in response to the pulling by the adjusting mechanism.

In an application, the longitudinal flexible member is configured to perform a therapy by relocating the patient's papillary muscle tissue.

In an application, the annuloplasty structure is configured to be implanted at an annulus of a mitral valve of the patient, and the apparatus is configured to be transcatheterally advanced toward the annulus.

In an application, the apparatus is configured to be transluminally advanced toward the annulus.

In an application, the second end portion of the longitudinal flexible member includes a tissue-coupling element.

In an application, the tissue-coupling element includes an anchor having at least one sharp portion.

There is further provided, in accordance with an application of the present invention, a method for use with a native valve of a heart of a patient, the native valve having a valve annulus, and the heart having a ventricle, the method including:

adjusting a dimension of the annulus by rotating a first adjusting mechanism of apparatus that has been implanted in the heart of the patient;

adjusting a first distance between a first portion of tissue of the ventricle of the patient and the annulus by rotating a second adjusting mechanism of the apparatus; and subsequently to the adjusting of the first distance, adjusting a second distance between a second portion of tissue of the ventricle of the patent and the annulus by rotating a third adjusting mechanism of the apparatus.

In an application, the annuloplasty structure has a first end and a second end, and a longitudinal axis therebetween, and sliding the second adjusting mechanism includes sliding the second adjusting mechanism along the longitudinal axis of the annuloplasty structure.

In an application:

the annuloplasty structure includes a body portion that defines a lumen therethrough, and a flexible longitudinal contracting member, having a first end portion, a second end portion, and a middle portion between the first and second end portions, at least one of the end portions being coupled to the first adjusting mechanism, and the middle portion being disposed within the lumen of the body portion, and adjusting the perimeter of the annuloplasty structure includes adjusting a length of the flexible longitudinal contracting member between the first end portion of the flexible longitudinal contracting member and the second end portion of the flexible longitudinal contracting member.

In an application, coupling the annuloplasty structure to the annulus includes coupling the annuloplasty structure to an annulus of a mitral valve of the patient such that the at least second adjusting mechanism is disposed in a vicinity of a fibrous trigone adjacent to the mitral valve.

In an application, the method further includes receiving information indicative of blood flow of the patent, subsequently to the adjusting of the first distance, and prior to the adjusting of the second distance.

In an application, the method further includes receiving information indicative of blood flow in the heart of the patient, subsequently to the adjusting of the dimension of the annulus, and prior to the adjusting of the first distance.

In an application, at least one of: (1) the adjusting of the dimension of the annulus, (2) the adjusting of the first distance, and (3) the adjusting of the second distance, include adjusting while the heart is beating.

In an application, adjusting the first adjusting mechanism includes adjusting the first adjusting mechanism while the heart of the patient is beating.

In an application, adjusting the at least second adjusting mechanism includes adjusting the at least second adjusting mechanism while the heart of the patient is beating.

In an application, coupling the second end portion to the first portion of the tissue of the ventricle includes coupling the second end portion to tissue of a papillary muscle of the patient.

In an application, the method further includes adjusting a dimension of the annulus by adjusting the first adjusting mechanism.

In an application, the method further includes adjusting a distance between the annulus and the tissue, by adjusting the second adjusting mechanism.

In an application, the method further includes adjusting a dimension of the annulus by adjusting the first adjusting mechanism, and adjusting a distance between the annulus and the tissue independently of the adjustment of the dimension of the annulus, by adjusting the second adjusting mechanism independently of the adjustment of the first adjusting mechanism.

In an application, coupling the second end portion to the tissue includes rotating an anchor coupled to the second end portion.

In an application, at least one selected from the group consisting of adjusting the first adjusting mechanism and adjusting the second adjusting mechanism, includes rotating a rotatable adjusting mechanism.

In an application, at least one action selected from the group consisting of adjusting the first adjusting mechanism and adjusting the second adjusting mechanism, includes reversibly adjusting.

In an application, coupling the annuloplasty structure to the annulus includes coupling a partial annuloplasty ring to the annulus.

In an application, coupling the annuloplasty structure to the annulus includes coupling a full annuloplasty ring to the annulus.

In an application, at least one action selected from the group consisting of adjusting the first adjusting mechanism and adjusting the second adjusting mechanism, includes adjusting using a rotation tool.

In an application, using the rotation tool includes using an elongate rotation tool that extends from outside the patient, to the apparatus.

In an application, the method further includes, prior to adjusting, performing at least one action selected from the group consisting of unlocking the first adjustment mechanism using the rotation tool, and unlocking the second adjustment mechanism using the rotation tool.

In an application, the method further includes transcatheterally advancing the annuloplasty structure to the native valve.

In an application, transcatheterally advancing the annuloplasty structure to the native valve includes transluminally advancing the annuloplasty structure to the native valve.

In an application, the annuloplasty structure is coupled to a third adjusting mechanism that is coupled to a first end portion of a second longitudinal flexible member, and the method further includes coupling a second end portion of the second longitudinal member to a second portion of the tissue of the ventricle.

In an application, the method further includes adjusting a distance between the annuloplasty structure and the second portion of the tissue by adjusting the third adjusting mechanism.

There is further provided, in accordance with an application of the present invention, a method for use with a native valve of a heart of a patient, the native valve having a valve annulus, and the heart having a ventricle, the method including:
while the heart is beating, using apparatus that has been implanted in the heart:
reducing a dimension of the annulus,
reducing a distance between the annulus and at least a first portion of tissue of the ventricle of the patient, and
subsequently, increasing at least one selected from the list consisting of: the dimension, and the distance; and
receiving information indicative of blood flow of the patient, the reducing and the increasing of the dimension and the distance being at least in part responsive to the receiving of the information.

In an application:
reducing the dimension includes rotating a first adjusting mechanism of the apparatus in a first rotational direction, and increasing the dimension includes rotating the first adjusting mechanism in a second, opposing rotational direction, and
reducing the distance includes rotating at least a second adjusting mechanism of the apparatus in a first rotational direction, and increasing the distance includes rotating the second adjusting mechanism in a second, opposing rotational direction.

There is further provided, in accordance with an application of the present invention, a method for use with a native valve of a heart of a patient, the native valve having a valve annulus, and the heart having a ventricle, the method including:
coupling, to the annulus, an annuloplasty structure, shaped to define a perimeter, and coupled to:
a first adjusting mechanism, configured to adjust the perimeter of the annuloplasty structure, and
at least a second adjusting mechanism, configured to be slidable around at least part of the perimeter of the annuloplasty structure, and coupled to a first end portion of at least one longitudinal flexible member;
coupling, to at least a first portion of tissue of the ventricle of the heart, a second end portion of the at least one longitudinal flexible member; and
sliding the second adjusting mechanism around at least part of the at least part of the perimeter of the annuloplasty structure.

In an application, the annuloplasty structure has a first end and a second end, and a longitudinal axis therebetween, and sliding the second adjusting mechanism includes sliding the second adjusting mechanism along the longitudinal axis of the annuloplasty structure.

In an application:
the annuloplasty structure includes a body portion that defines a lumen therethrough, and a flexible longitudinal contracting member, having a first end portion, a second end portion, and a middle portion between the first and second end portions, at least one of the end portions being coupled to the first adjusting mechanism, and the middle portion being disposed within the lumen of the body portion, and
adjusting the perimeter of the annuloplasty structure includes adjusting a length of the flexible longitudinal contracting member between the first end portion of the flexible longitudinal contracting member and the second end portion of the flexible longitudinal contracting member.

In an application, coupling the annuloplasty structure to the annulus includes coupling the annuloplasty structure to an annulus of a mitral valve of the patient such that the at least second adjusting mechanism is disposed in a vicinity of a fibrous trigone adjacent to the mitral valve.

In an application, coupling the annuloplasty structure to the annulus includes coupling a partial annuloplasty ring to the annulus.

In an application, coupling the annuloplasty structure to the annulus includes coupling a full annuloplasty ring to the annulus.

In an application, adjusting the first adjusting mechanism includes adjusting the first adjusting mechanism while the heart of the patient is beating.

In an application, adjusting the at least second adjusting mechanism includes adjusting the at least second adjusting mechanism while the heart of the patient is beating.

In an application, coupling the second end portion to the first portion of the tissue of the ventricle includes coupling the second end portion to tissue of a papillary muscle of the patient.

In an application, the method further includes adjusting a dimension of the annulus by adjusting the first adjusting mechanism.

In an application, the method further includes adjusting a distance between the annulus and the tissue, by adjusting the second adjusting mechanism.

In an application, the method further includes adjusting a dimension of the annulus by adjusting the first adjusting mechanism, and adjusting a distance between the annulus and the tissue independently of the adjustment of the dimension of the annulus, by adjusting the second adjusting mechanism independently of the adjustment of the first adjusting mechanism.

In an application, coupling the second end portion to the tissue includes rotating an anchor coupled to the second end portion.

In an application, at least one selected from the group consisting of adjusting the first adjusting mechanism and adjusting the second adjusting mechanism, includes rotating a rotatable adjusting mechanism.

In an application, at least one action selected from the group consisting of adjusting the first adjusting mechanism and adjusting the second adjusting mechanism, includes reversibly adjusting.

In an application, at least one action selected from the group consisting of adjusting the first adjusting mechanism and adjusting the second adjusting mechanism, includes adjusting using a rotation tool.

In an application, using the rotation tool includes using an elongate rotation tool that extends from outside the patient, to the apparatus.

In an application, the method further includes, prior to adjusting, performing at least one action selected from the group consisting of unlocking the first adjustment mechanism using the rotation tool, and unlocking the second adjustment mechanism using the rotation tool.

In an application, the method further includes transcatheterally advancing the annuloplasty structure to the native valve.

In an application, transcatheterally advancing the annuloplasty structure to the native valve includes transluminally advancing the annuloplasty structure to the native valve.

In an application, the annuloplasty structure is coupled to a third adjusting mechanism that is coupled to a first end portion of a second longitudinal flexible member, and the method further includes coupling a second end portion of the second longitudinal member to a second portion of the tissue of the ventricle.

In an application, the method further includes adjusting a distance between the annuloplasty structure and the second portion of the tissue by adjusting the third adjusting mechanism.

There is further provided, in accordance with an application of the present invention, apparatus for use with a native valve of a heart of a patient, the native valve having a valve annulus, and the heart having a ventricle, the apparatus including:

an annuloplasty structure, shaped to define a perimeter, and configured to be disposed at the annulus of the native valve of the patient;

a first adjusting mechanism, coupled to the annuloplasty structure, and configured to adjust the perimeter of the annuloplasty structure;

at least one longitudinal flexible member, having a first end portion, and a second end portion that is configured to be coupled to tissue of the ventricle of the heart of the patient; and at least a second adjusting mechanism, coupled to the annuloplasty structure and to the first end portion of the at least one longitudinal flexible member, and configured to adjust a distance between the second adjusting mechanism and the second end portion of the at least one longitudinal flexible member, the first and second adjusting mechanisms each including a respective locking mechanism, each locking mechanism:
  having an unlocked state in which the respective adjusting mechanism is adjustable, having
  having a locked state in which the locking mechanism inhibits adjustment of the respective adjusting mechanism, and
  configured to be intracorporeally moved from the locked state to the unlocked state.

In an application, the annuloplasty structure includes a partial annuloplasty ring.

In an application, the annuloplasty structure includes a full annuloplasty ring.

In an application, the annuloplasty structure is coated with polytetrafluoroethylene.

In an application:
  the annuloplasty structure is configured to be implanted at an annulus of a mitral valve of the patient,
  the at least second adjusting mechanism is configured to be coupled to a location along the annulus, in a vicinity of a fibrous trigone adjacent to the mitral valve.

In an application, the apparatus further includes a plurality of sutures, each suture of the plurality of sutures being configured to be fastened to a respective location along a circumference of an annulus of a mitral valve of the patient, the plurality of sutures being configured to facilitate advancement of the annuloplasty structure toward the annulus.

In an application, the annuloplasty structure includes a coiled structure having a lumen.

In an application, the annuloplasty structure has a first end and a second end, and a longitudinal axis therebetween, and the second adjusting mechanism is movable along the longitudinal axis of the annuloplasty structure.

In an application, the annuloplasty structure includes a body portion that defines a lumen therethrough, and the annuloplasty structure further includes a flexible longitudinal contracting member, having a first end portion, a second end portion, and a middle portion between the first and second end portions, at least one of the end portions being coupled to the first adjusting mechanism, and the middle portion being disposed within the lumen of the body portion.

In an application, the first adjusting mechanism is movably coupled to the annuloplasty structure.

In an application, the first adjusting mechanism is configured to reversibly adjust the perimeter of the annuloplasty structure, and the second adjusting mechanism is configured to reversibly adjust the distance.

In an application, the second adjusting mechanism is configured to adjust the distance between the second adjusting mechanism and the second end portion of the at least one longitudinal flexible member, independently of the adjusting of the perimeter of the annuloplasty structure by the first adjusting mechanism.

In an application:
  the at least one longitudinal flexible member includes a first longitudinal flexible member and a second longitudinal flexible member, the first and second longitudinal members each having a first end portion and a second end portion, the second portion of the first longitudinal flexible member being configured to be coupled to a first portion of the tissue, and the second portion of the second longitudinal flexible member being configured to be coupled to a second portion of the tissue,
  the second adjusting mechanism is coupled to the first end portion of the first longitudinal flexible member, and is configured to adjust a distance between the second adjusting mechanism and the second end portion of the first longitudinal flexible member,
  the apparatus further includes a third adjusting mechanism, coupled to the annuloplasty structure and to the first end portion of the second longitudinal flexible member, and is configured to adjust a distance between the third adjusting mechanism and the second end portion of the second longitudinal flexible member.

In an application:
at least one selected from the group consisting of the first portion of the tissue and the second portion of the tissue, includes tissue of a papillary muscle of the patient, and
at least one selected from the group consisting of the second adjusting mechanism and the third adjusting mechanism, is configured to adjust a distance between the papillary muscle and the annuloplasty structure.

In an application, the third adjusting mechanism is configured to adjust the distance between the third adjusting mechanism and the second end portion of the second longitudinal flexible member, independently of the adjustment, by the second adjusting mechanism, of the distance between the second adjusting mechanism and the second end portion of the first longitudinal flexible member.

In an application, the first adjusting mechanism includes a first rotatable adjusting mechanism, and the second adjusting mechanism includes a second rotatable adjusting mechanism.

In an application, the first rotatable adjusting mechanism and the second rotatable adjusting mechanism are both rotatable bidirectionally.

In an application, the second rotatable adjusting mechanism includes a spool, and the spool is configured to pull the tissue toward the annuloplasty structure, via the longitudinal flexible member, responsively to rotation of the spool.

In an application, the apparatus further includes a rotation tool, configured to rotate the first rotatable adjusting mechanism.

In an application, the rotation tool includes an elongate rotation tool, configured to extend from outside the patient, to the first rotatable adjusting mechanism.

In an application, the rotation tool is configured to facilitate adjustment of the first adjusting mechanism while the heart of the patient is beating.

In an application, the rotation tool includes a first rotation tool, and the apparatus further includes a second rotation tool, configured to rotate the second rotatable adjusting mechanism.

In an application, the first rotation tool is configured to intracorporeally move the first rotatable adjusting mechanism into the unlocked configuration thereof, and the second rotation tool is configured to intracorporeally move the second rotatable adjusting mechanism into the unlocked configuration thereof.

In an application, the tissue includes papillary muscle tissue of the patient, and apparatus is configured to relocate the papillary muscle tissue, by pulling the papillary muscle tissue toward the annuloplasty structure.

In an application:
the annuloplasty structure is configured to be implanted at an annulus of a mitral valve of the patient, and
the longitudinal flexible member is configured to relocate the papillary muscle tissue, in response to the pulling by the adjusting mechanism.

In an application, the longitudinal flexible member is configured to perform a therapy by relocating the patient's papillary muscle tissue.

In an application, the annuloplasty structure is configured to be implanted at an annulus of a mitral valve of the patient, and the apparatus is configured to be transcatheterally advanced toward the annulus.

In an application, the apparatus is configured to be transluminally advanced toward the annulus.

In an application, the second end portion of the longitudinal flexible member includes a tissue-coupling element.

In an application, the tissue-coupling element includes an anchor having at least one sharp portion.

There is further provided, in accordance with an application of the present invention, apparatus for use with a native valve of a heart of a patient, the native valve having a valve annulus, and the heart having a ventricle, the apparatus including:
an annuloplasty structure, configured to be disposed at the annulus of the native valve of the patient, and shaped to define a perimeter;
a perimeter-adjusting mechanism, coupled to the annuloplasty structure, and configured to adjust the perimeter of the annuloplasty structure; and
at least two longitudinal flexible members, each longitudinal flexible member having a first end portion and a second end portion, the second end portion of each longitudinal flexible member being configured to be coupled to a respective portions of tissue of a ventricle of the heart of the patient; and
at least two length-adjusting mechanisms, each being coupled to the annuloplasty structure and to the first end portion of a respective longitudinal flexible member, and configured to adjust a distance between the length-adjusting mechanism and the second end portion of the respective longitudinal flexible member, independently of the adjustment of the perimeter of the annuloplasty structure by the first adjusting mechanism.

In an application:
the at least two length-adjusting mechanisms include a first length-adjusting mechanism and a second length-adjusting mechanism,
the at least two longitudinal flexible members include a first longitudinal flexible member and a second longitudinal flexible member,
the first length-adjusting mechanism is coupled to the first end portion of the first longitudinal flexible member, and is configured to adjust the distance between the first length-adjusting mechanism and the second end portion of the first longitudinal flexible member, and
the second length-adjusting mechanism is coupled to the first end portion of the second longitudinal flexible member, and is configured to adjust a distance between the second length-adjusting mechanism and the second end portion of the second longitudinal flexible member, independently of the adjustment, by the first length-adjusting member, of a distance between the first length-adjusting mechanism and the second end portion of the first longitudinal flexible member.

In an application, at least one of the length-adjusting mechanisms is movable around at least part of the perimeter of the annuloplasty structure.

In an application, the annuloplasty structure includes a body portion that defines a lumen therethrough, and the annuloplasty structure further includes a flexible longitudinal contracting member, having a first end portion, a second end portion, and a middle portion between the first and second end portions, at least one of the end portions being coupled to the first adjusting mechanism, and the middle portion being disposed within the lumen of the body portion.

There is further provided, in accordance with an application of the present invention, a method, including:
providing an annuloplasty structure, the annuloplasty structure including:
at least one adjusting mechanism couplable to the annuloplasty structure; and
at least one longitudinal flexible member;

coupling the annuloplasty structure to an annulus of a mitral valve of a patient;

coupling the longitudinal flexible member to a portion of tissue; and relocating the portion of tissue toward the annulus by pulling the tissue with the adjusting mechanism, via the longitudinal flexible member.

In an application, coupling the longitudinal flexible member to the portion of tissue includes coupling the longitudinal flexible member to papillary muscle tissue.

In an application, the annuloplasty structure includes two adjusting mechanisms, each adjusting mechanism configured to relocate respective portions of tissue, and coupling the annuloplasty structure to the annulus includes:

coupling a first one of the adjusting mechanisms to a first location along the annulus in a vicinity of a first fibrous trigone of the mitral valve; and coupling a second one of the adjusting mechanisms to a second location along the annulus in a vicinity of a second fibrous trigone of the mitral valve.

In an application, the method further includes transcatheterally advancing the annuloplasty structure to the annulus.

In an application, coupling the annuloplasty structure to the annulus includes coupling the annuloplasty structure to the annulus during open heart surgery.

In an application, the method further includes:

rotating, in a first direction, a rotatable adjusting mechanism that is coupled to the annuloplasty structure, by pulling a contracting member that is coupled to the rotatable structure; and responsively, drawing first and second portions of the annuloplasty structure toward each other.

The present invention will be more fully understood from the following detailed description of embodiments thereof, taken together with the drawings, in which:

BRIEF DESCRIPTION OF THE DRAWINGS

FIG. 5 is a schematic illustration of another annuloplasty structure coupled to at least first and second adjusting mechanisms, in accordance with some applications of the present invention;

FIGS. 9A-B are schematic illustrations of an implant structure comprising a septo-lateral adjusting mechanism, in accordance with some applications of the present invention;

FIG. 11 is a schematic illustration of a system for providing information indicative of heart function of the patient, and for facilitating adjusting the adjusting mechanisms of an annuloplasty structure in response to the information, in accordance with some applications of the invention.

DETAILED DESCRIPTION OF EMBODIMENTS

Figure 1:
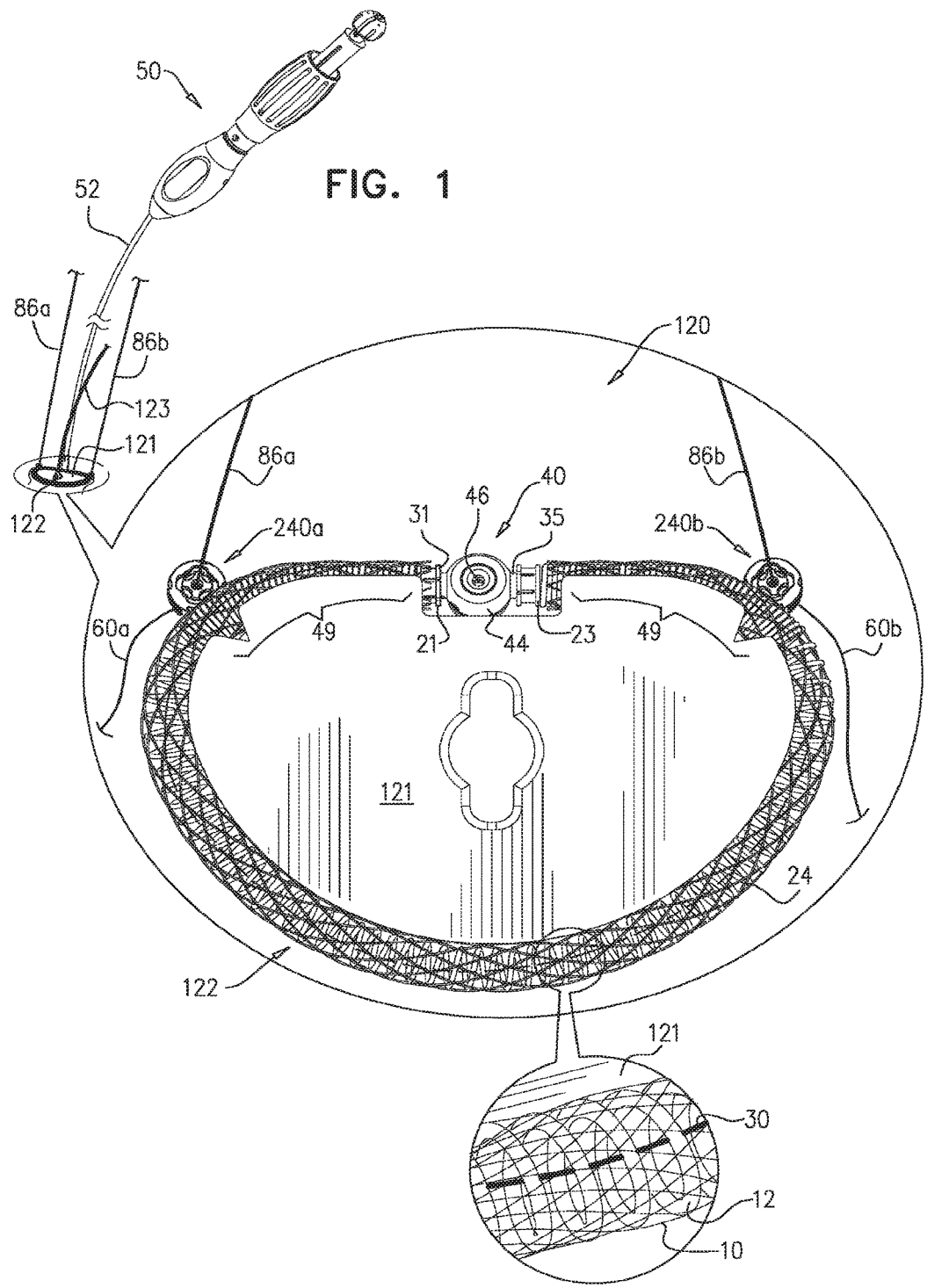
FIG. 1 is a schematic illustration of an annuloplasty structure coupled to at least first and second adjusting mechanisms, in accordance with some applications of the present invention.

Reference is now made to FIG. 1, which is a schematic illustration of a system 120 comprising an implant structure 122 which comprises an adjustable annuloplasty ring structure that is coupled to two or more flexible-longitudinal-tension-member-adjusting-mechanisms 240 (e.g., flexible-longitudinal-tension-member-adjusting-mechanisms 240a and 240b), in accordance with some applications of the present invention. For some applications, as shown, the annuloplasty ring structure comprises a full annuloplasty ring. Adjusting mechanisms 240a and 240b typically comprise rotatable structures (e.g., spools, as described hereinbelow) which are coupled to respective first portions of flexible longitudinal tension members 60a and 60b. When system, 120 is implanted in the heart of the patient, implant structure 122 is configured to be implanted at an annulus of a native valve of a patient (e.g., an atrioventricular valve such as the mitral valve or the tricuspid valve). Tension members 60a and 60b are configured to extend toward the ventricle of the heart of the patient by passing between the leaflets of the valve or by passing through tissue of the annulus or commissures of the valve. Respective second end portions of tension members 60a and 60b are configured to be coupled to respective portions of cardiac tissue which are in the vicinity of the ventricle of the heart (e.g., portions of papillary muscle, portions of tissue at the base of the papillary muscle, portions of tissue in a vicinity of the apex, portions of tissue of an inner wall of the ventricle, and/or portions of tissue of an outer wall of the ventricle). Rotation of the rotatable structures of mechanisms 240a and 240b in a first rotational direction pulls tight the respective tension members 60a and 60b in order to draw the portions of cardiac tissue toward implant structure 122 (i.e., by reducing a distance between each mechanism 240 and the second end portion of the respective tension member 60). Rotation of the rotatable structures in a second, opposing, rotational direction loosens the respective tension members. For some applications of the present invention, system 120 functions to repair and/or effect remodeling of the portions of cardiac tissue, remodeling of the papillary muscles, and/or remodeling of a heart wall of the ventricle to treat distension. For some applications, tension members function as artificial chordae tendineae.

Flexible tension members 60a and 60b comprise a wire, a ribbon, a rope, or a band, comprising a flexible metal. Typically, flexible tension members 60a and 60b comprise a flexible and/or superelastic material, e.g., nitinol, polyester, stainless steel, or cobalt chrome. In some applications of the present invention, flexible tension members 60a and 60b each comprise a braided polyester suture (e.g., Ti-Cron™). In some applications of the present invention, flexible contracting members 60a and 60b are coated with polytetrafluoroethylene (PTFE). In some applications of the present invention, flexible tension member 60a and 60b each comprise a plurality of wires that are intertwined to form a rope structure.

Typically, but not necessarily, each of adjusting mechanisms 240a and 240b is coupled to a respective longitudinal guide member 86a and 86b. Distal end portions of each guide member 86a and 86b are coupled to respective portions of mechanisms 240a and 240b and facilitate guiding along members 86a and 86b of a rotational tool toward the rotatable structures of mechanisms 240a and 240b.

The annuloplasty structure of implant structure 122 is shaped to define a flexible, tubular body portion 24 that is shaped so as to define a lumen along a longitudinal axis of structure 122 that houses at least part of at least one flexible longitudinal contracting member 30 (e.g., a middle portion of member 30). At least a portion, e.g., the entirety, of body portion 24 comprises a compressible material (e.g., a coiled element 12), as shown by way of illustration and not limitation. For example, body portion 24 may comprise stent-like struts, or a braided mesh (independently of coiled portion 12). Typically, coiled element 12 is surrounded by a braided mesh 10.

Typically, body portion 24 comprises a flexible biocompatible material, e.g., nitinol, stainless steel, platinum iridium, titanium, expanded polytetrafluoroethylene (ePTFE), or cobalt chrome. In some applications of the present invention, body portion 24 is coated with PTFE (Polytetrafluoroethylene). In other applications of the present invention, body portion 24 comprises accordion-like compressible structures which facilitate proper cinching of the annulus when structure 122 is contracted. Body portion 24, when compressed, e.g., typically along a longitudinal axis of structure 122, enables portions of annuloplasty structure 122 to contract and independently conform to the configuration of the annulus of the mitral valve of a given subject. Thus, the compressible element of body portion 24 facilitates contraction of the annulus in response to contraction of structure 122.

The annuloplasty structure of implant structure 122 comprises a flexible-longitudinal-contracting-member-adjusting-mechanism 40 disposed within a housing 44 and coupled to contracting member 30 (as described hereinbelow with reference to FIG. 3). Adjusting mechanism 40 is configured to adjust a degree of tension of contracting member 30 in order to adjust a perimeter of implant structure 122. Adjusting mechanism 40 thereby acts as a perimeter-adjusting mechanism. Housing 44 of adjusting mechanism 40 is shaped so as to define first and second coupling members 31 and 35 (shown in FIG. 3). Body portion 24 has first and second ends 21 and 23 which are coupled to first and second coupling members 31 and 35, and thereby to adjusting mechanism 40, in order to create a full annuloplasty ring. Thus, adjusting mechanism 40 is aligned with body portion 24 along the longitudinal axis thereof.

Adjusting mechanisms 240a and 240b are coupled to an outer surface of body portion 24, as shown. Typically, mechanisms 240a and 240b are coupled via sutures or any other mechanical coupling, as described hereinbelow with reference to FIGS. 2A-B. Typically, for applications in which structure 122 is implanted on the annulus of a mitral valve, adjusting mechanism 240a is coupled to a portion of the annuloplasty structure in a vicinity thereof that is configured to be placed on or near a left fibrous trigone of the annulus of the mitral valve of the patient, and adjusting mechanism 240b is coupled to a portion of the annuloplasty structure in a vicinity thereof that is configured to be placed on or near a right fibrous trigone of the annulus of the mitral valve of the patient.

Flexible contracting member 30 comprises a wire, a ribbon, a rope, or a band, comprising a flexible metal. Flexible contracting member 30 is coupled at a first end portion thereof to flexible-longitudinal-contracting-member-adjusting-mechanism 40 which is coupled to a first end 21 of body portion 24. A second end portion of flexible contracting member 30 is coupled to a second end 23 of body portion 24. Typically, during a resting state of structure 122, flexible contracting member 30 (e.g., the middle portion thereof) is disposed in parallel with the longitudinal axis of structure 122. Flexible member 30, for some applications does not comprise a continuous band that runs through the entire lumen of the annuloplasty devices described herein, and flexible member 30 has at least one free end portion.

Typically, flexible contracting member 30 comprises a wire, a cable, or a rope, and taken together with the compressible element of body portion 24 and the braided mesh surrounding body portion 24, imparts flexibility to the entire annuloplasty structure.

Typically, flexible contracting member 30 comprises a flexible and/or superelastic material, e.g., nitinol, polyester, stainless steel, or cobalt chrome, and is configured to reside chronically within structure 122. In some applications of the present invention, flexible contracting member 30 comprises a braided polyester suture (e.g., Ti-Cron™). In some applications of the present invention, flexible contracting member 30 is coated with polytetrafluoroethylene (PTFE). In some applications of the present invention, flexible contracting member 30 comprises a plurality of wires that are intertwined to form a rope structure.

Adjusting mechanism 40 comprises a housing 44 which houses a rotatable structure, or a spool 46. The rotatable structure is rotatable in first and second opposing rotational directions with respect to housing 44 so as to expand and contract the annuloplasty structure, respectively. Spool 46 has a cylindrical body that is disposed perpendicularly with respect to the longitudinal axis of structure 122. As shown in FIG. 3, spool 46 is shaped to provide at least one hole 42 for coupling of the first end portion of flexible contracting member 30 thereto and, thereby, to adjusting mechanism 40. For some applications of the present invention, spool 46 is shaped to define one or more holes 42 configured for looping a portion of contracting member 30 therethrough, as described hereinbelow. In such an application: (a) a middle portion, which defines the first end portion, of contracting member 30 is coupled to spool 46 by being looped through one or more holes 42, (b) first and second portions that extend from the first end portion looped through spool 46 extend toward second end 23 of structure body portion 24, and (c) first and second free ends of contracting member 30 are coupled to second end 23 of body portion 24 and define a second end portion of contracting member 30.

It is to be noted that for some applications of the present invention, flexible contracting member 30 may be coupled at both its first and second end portions, e.g., first and second ends, to spool 46 of adjusting mechanism 40. In some applications of the present invention, a first end of flexible contracting member 30 is coupled to spool 46 while a second end of flexible contracting member 30 is coupled to the housing which houses spool 46. For some applications, contracting member 30 comprises a continuous band that is looped through a portion of spool 46.

As shown, the annuloplasty structure of implant structure 122 defines a substantially ring-shaped configuration, e.g., a "D"-shaped configuration, as shown, which conforms to the shape of the annulus of a mitral valve of the subject. For applications in which structure 122 is implanted at a tricuspid valve of the patient, the annuloplasty structure assumes a shape suitable to fit the tricuspid valve (e.g., a substantially oval shape).

Prior to contracting of structure 122, the compressible element of body portion 24 is relaxed and structure 122 defines a first perimeter thereof. Structure 122 provides portions 49 which are flexible and less longitudinally compressible, e.g., not longitudinally compressible, with respect to the compressible element of body portion 24. Portions 49 are configured to be disposed along the fibrous portion of the annulus that is between the fibrous trigones of the mitral valve of the heart when structure 122 is anchored, sutured, fastened or otherwise coupled to the annulus of the mitral valve. Portions 49 impart rigidity to structure 122 in the portion thereof that is disposed between the fibrous trigones such that structure 122 better mimics the conformation and functionality of the mitral valve. That is, during rotation of spool 46, and the concurrent contraction or expansion of structure 122, energy is not expended on contracting or expanding portions 49. As shown, coiled portion 12 of body portion 24 has a very small pitch compared to coiled portion 12 in the remaining portions of the annuloplasty structure. For some applications, portions 49 comprise a material that is arranged in a configuration in which portions 49 are more rigid.

Typically, both portions 49 have a combined length of 10-50 mm.

Thus, the annuloplasty structure of implant structure 122 defines a compressible portion and a non-compressible portion. Typically, a radius of curvature at a center of the compressible portion of body portion 24 is smaller than a radius of curvature at a center of less-compressible portions 49, when no external force is applied to the annuloplasty structure.

It is to be noted that the compressible element of body portion 24 and less-compressible portions 49 comprise flexible coiled elements by way of illustration and not limitation. For example, the compressible element of body portion 24 and less-compressible portions 49 may comprise stent-like struts, or a braided mesh. In either configuration, portions 49 are chronically longitudinally compressed in a resting state of structure 122.

It is to be noted that, structure 122 may be provided independently of less-compressible portions 49. In such applications of the present invention, the annuloplasty structure comprises a fully compressible ring, e.g., a continuous ring.

It is to be noted that housing 44 (and mechanism 40) may be disposed at any suitable location along structure 122, and not only in between portions 49 (e.g., in a portion of the annuloplasty structure designated for implantation at an anterior portion of the mitral valve). For example, housing 44 may be coupled to the section of body portion 24 that is compressible. In some applications of the present invention, housing 44 may be disposed in the middle of the section of body portion 24 that is compressible. In some applications of the present invention, housing 44 may be coupled to structure 122 at an interface between a first end of portion 49 and the section of body portion 24 that is compressible. In such applications of the present invention, portions 49 may be combined to form one substantially less-compressible portion having first and second ends that are in series with the compressible portion of body portion 24. For some applications, a plurality of housings and adjusting mechanisms 40 described herein may be coupled to the annuloplasty structure. Each adjusting mechanism 40 may be coupled to a respective contracting member 30 which controls a respective portion of the annuloplasty structure.

Typically, the annuloplasty structure of implant structure 122 is delivered to the annulus of the valve using an elongate tool 50 that is reversibly coupled to adjusting mechanism 40 of structure 122. Tool 50 comprises an elongate body portion 52 which houses a flexible rod that is coupled at a distal end thereof to a screwdriver head. The screwdriver head is configured to be disposed within the channel of spool 46. Typically, the rod functions as a screwdriver which applies force to the screwdriver head in order to rotate spool 46, and thereby facilitate contraction of structure 122.

For some applications, the screwdriver head comprises force applicator 88, as described hereinabove with reference to FIG. 3. For other applications, force applicator 88 is coupled to an elongate member that is removable from spool 46 by tool 50.

(In this context, in the specification and in the claims, "proximal" means closer to the orifice through which the implant structure is originally placed into the body of the patient, along the path of delivery of the implant structure, and "distal" means further from this orifice along the path of delivery of the implant structure.)

In some applications of the present invention, the annuloplasty structure is wrapped around an annuloplasty sizer 121. Once wrapped around sizer 121, the flexible member is contracted by tool 50 such that the annuloplasty structure hugs and is stabilized around sizer 121. Sizer is coupled to a shaft 123. (It is to be noted that, for clarity of illustration, tool 50, body portion 52, and shaft 123 are not shown in the enlarged portion of FIG. 1.) Tool 50, shaft 123, and sizer 121 help position implant structure 122 along the annulus and stabilize the structure as it is being contracted. Once the structure 122 is positioned at the annulus, structure is sutured, anchored, or otherwise coupled to the annulus. Following the coupling of structure 122 to the annulus, sizer 121 is decoupled from structure 122.

Subsequently, tool 50 facilitates the contraction and/or expansion of the annuloplasty structure of implant structure 122 in order to adjust a dimension of the valve annulus. The distal portion of tool 50 comprises a tool housing which surrounds a portion of housing 44 of mechanism 40, and stabilizes housing 44 during the advancement and contraction and/or expansion of structure 122.

Figure 2A:
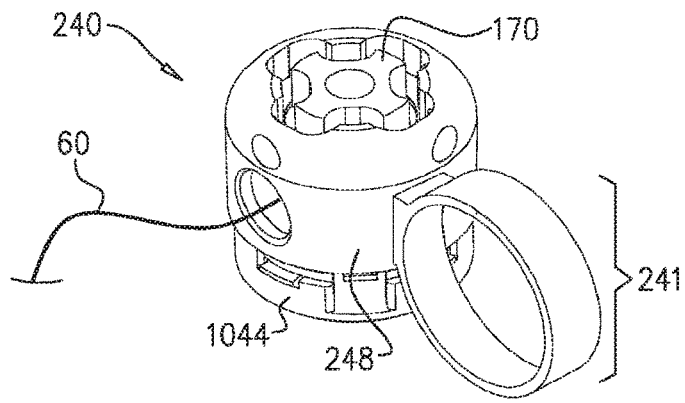
FIGS. 2A-B are schematic illustrations of an adjustable annuloplasty structure coupled to adjusting mechanisms that are slidable with respect to the adjustable annuloplasty structure, in accordance with some applications of the present invention.
Figure 2B:
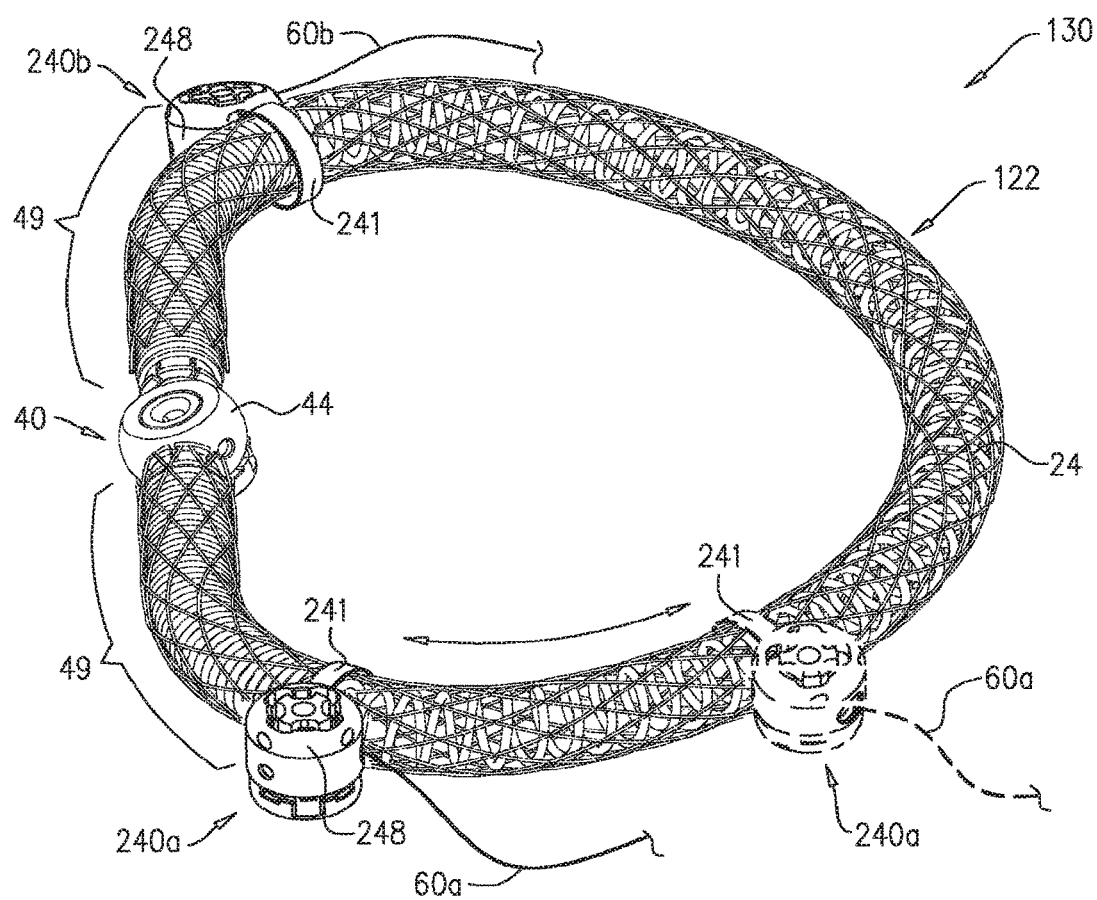

Reference is now made to FIGS. 2A-B, which are schematic illustrations of a system 130, which is similar to system 120, as described hereinabove with reference to FIG. 1, with the exception that adjusting mechanisms 240a and 240b are coupled to body portion 24 of the annuloplasty structure of implant structure 122 by a slide-facilitating ring 241, in accordance with some applications of the present invention. Housing 248 of each adjusting mechanism 240 is coupled to ring 241, as shown in FIG. 2A. Ring 241 surrounds a portion of the outer surface of body portion 24 and enables mechanism 240 to slide along the outer surface of body portion 24 to any suitable position along the annuloplasty structure of implant structure 122 (as indicated by the arrow and the adjusting mechanism 240 shown in phantom in FIG. 2B).

It is to be noted that adjusting mechanisms 240 are shown in FIGS. 2A-B without guide members 86 (described hereinabove with reference to FIG. 1).

Figure 3:
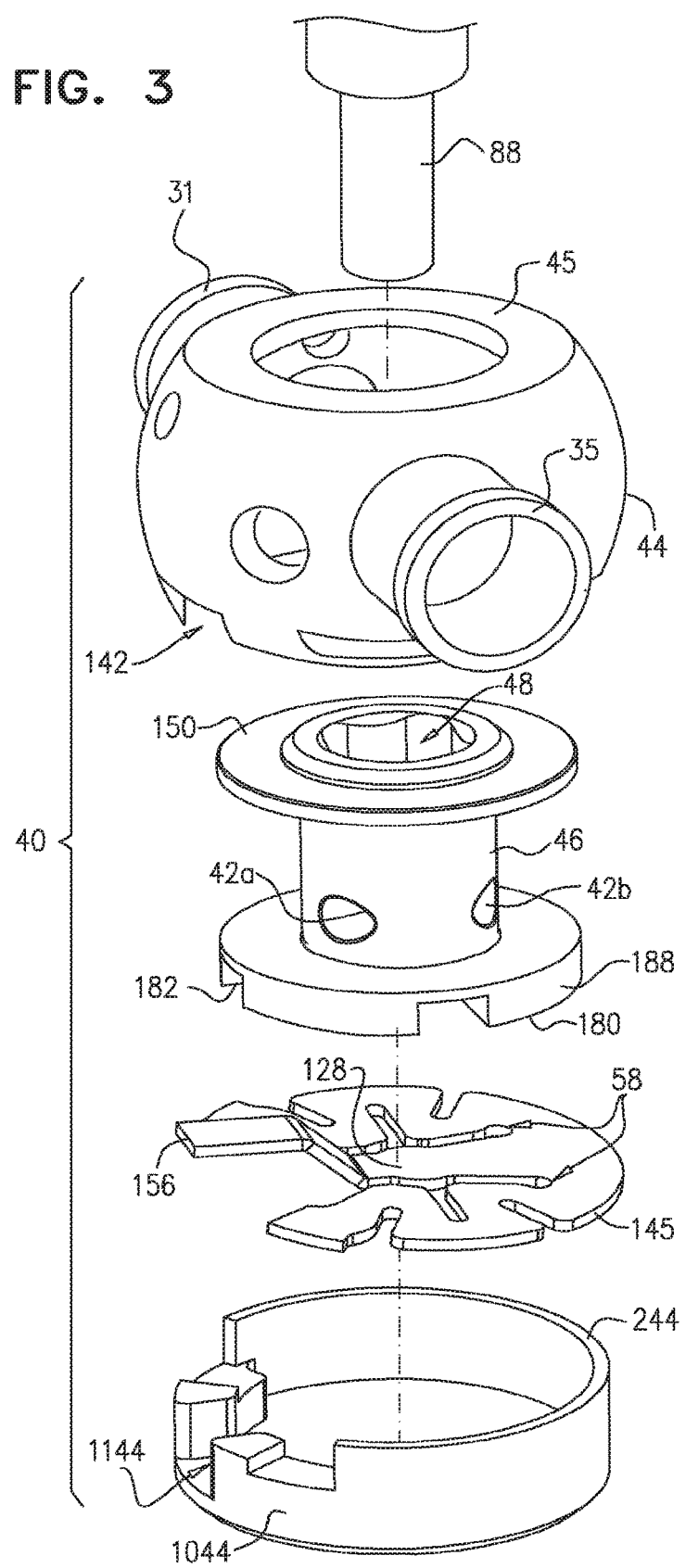
FIG. 3 is a schematic illustration of an adjusting mechanism, in accordance with some applications of the present invention.

Reference is now made to FIG. 3, which is a schematic illustration showing a relationship among individual components of flexible-longitudinal-contracting-member-adjusting-mechanism 40, in accordance with some applications of the present invention. Adjusting mechanism 40 is shown as comprising spool housing 44 which defines an upper surface 45 and a recess 142 at a lower surface thereof. A spool 46 is configured to be disposed within housing 44 and defines an upper surface 150, a lower surface 180, and a cylindrical body portion disposed vertically between surfaces 150 and 180. The cylindrical body portion of spool 46 is shaped so as to define a channel which extends from a first opening at upper surface 150 to a second opening at lower surface 180.

Lower surface 180 of spool 46 is shaped to define one or more (e.g., a plurality, as shown) of recesses 182 which define structural barrier portions 188 of lower surface 180. It is to be noted that any suitable number of recesses 182 may be provided, e.g., between 1 and 10 recesses. For some applications, recesses 182 are provided circumferentially with respect to lower surface 180 of spool 46.

Typically, spool 46 comprises a locking mechanism 145. For some applications, locking mechanism 145 is coupled, e.g., welded, at least in part to a lower surface of spool housing 44. Typically, locking mechanism 145 defines a mechanical element having a planar surface that defines slits 58. The surface of locking mechanism 145 may also be curved, and not planar. Locking mechanism 145 is shaped to provide a protrusion 156 which projects out of a plane defined by the planar surface of the mechanical element. The slits define a depressible portion 128 of locking mechanism 145 that is disposed in communication with and extends toward protrusion 156.

In a resting state of locking mechanism 145 (i.e., a locked state of spool 46), protrusion 156 is disposed within a recess 182 of spool 46. Additionally, in the locked state of spool 46, protrusion 156 is disposed within recess 142 of housing 44.

Depressible portion 128 is aligned with the opening at lower surface 180 of spool 46 and is moveable in response to a force applied thereto by a distal force applicator 88. That is, distal force applicator 88 is configured to be disposed within the channel of spool 46. A distal end of applicator 88 is configured to push on depressible portion 128 in order to move depressible portion 128 downward so as to disengage protrusion 156 from within a recess 182 of spool and to unlock spool 46 from locking mechanism 145.

It is to be noted that the planar, mechanical element of locking mechanism 145 is shown by way of illustration and not limitation and that any suitable mechanical element having or lacking a planar surface but shaped to define at least one protrusion may be used together with locking mechanism 145.

A cap 1044 is provided that is shaped so as to define a planar surface and an annular wall having an upper surface 244 that is coupled to, e.g., welded to, the lower surface of spool housing 44. The annular wall of cap 1044 is shaped so as to define a recessed portion 1144 of cap 1044 that is in alignment with recess 142 of spool housing 44. Locking mechanism 145 is disposed between lower surface 180 of spool 46 and the planar surface of cap 1044.

In an unlocked state of adjusting mechanism 40, protrusion 156 of locking mechanism 145 is disposed within recessed portion 1144 of cap 1044. In the unlocked state, force applicator 88 extends through spool 46 and pushes against depressible portion 128 of locking mechanism 145. The depressible portion is thus pressed downward, freeing protrusion 156 from within a recess 182 defined by structural barrier portions 188 of the lower portion of spool 46. Additionally, protrusion 156 is freed from within the recessed portion of spool housing 44. As a result, contracting mechanism 40 is unlocked, and spool 46 may be rotated with respect to spool housing 44.

Cap 1044 functions to restrict distal pushing of depressible portion 128 beyond a desired distance so as to inhibit deformation of locking mechanism 145. For applications in which adjusting mechanism 40 is implanted in heart tissue, cap 1044 also provides an interface between adjusting mechanism 40 and the heart tissue. This prevents interference of heart tissue on adjusting mechanism 40 during the locking and unlocking thereof. Additionally, cap 1044 prevents damage to heart tissue by depressible portion 128 as it is pushed downward.

Spool 46 is shaped so as to define a driving interface 48. A rotation tool (not shown) is configured to slide engage spool 46 at interface 48. The rotation tool is configured to rotate spool 46 by applying rotational force to spool 46 at interface 48. For some applications, a friction-reducing ring (not shown in FIG. 3, but shown in FIG. 4) is disposed between upper surface 150 of spool 46 and the inner surface of upper surface 45 of spool housing 44.

For some applications the rotation tool used to rotate spool 46 may be shaped to provide distal force applicator 88 configured to unlock spool 46 from locking mechanism 145. When unlocked, spool 46 may be bidirectionally rotated.

Following rotation of spool 46 such that contraction member 30 is contracted sufficiently to adjust the perimeter of the annuloplasty structure to a desired dimension so as to contract the annulus of the valve, spool 46 is then locked in place so as to restrict rotation of spool 46. Force applicator 88 is removed from within the channel of spool 46, and thereby, depressible portion 128 returns to its resting state. As depressible portion 128 returns to its resting state, protrusion 156 is introduced within one of the plurality of recesses 182 of lower surface 180 of spool 46 and within recess 142 of housing 44, and thereby restricts rotation of spool 46.

Figure 4:
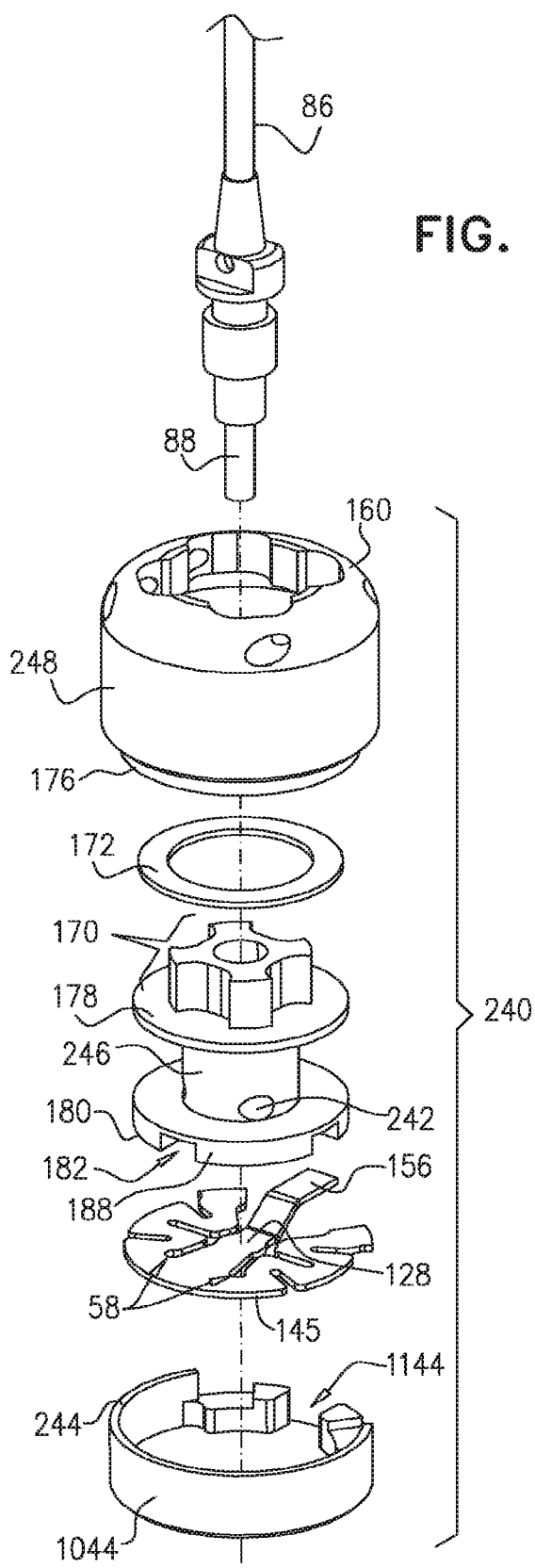
FIG. 4 is a schematic illustration of another adjusting mechanism, in accordance with some applications of the present invention.

Reference is now made to FIG. 4, which is a schematic illustration showing a relationship among individual components of flexible-longitudinal-tension-member-adjusting-mechanism 240, in accordance with some applications of the present invention. Adjusting mechanism 240 is shown as comprising spool housing 248 which defines an upper surface 160 and a lower surface 176 defining a recessed portion (as described with regard to recess 142 with reference to FIG. 3). A spool 246 is configured to be disposed within housing 248 and defines an upper surface 178, a lower surface 180, and a cylindrical body portion disposed vertically between surfaces 178 and 180. The cylindrical body portion of spool 246 is shaped so as to define a channel which extends from a first opening at upper surface 178 to a second opening at lower surface 180.

Lower surface 180 of spool 246 is shaped to define one or more (e.g., a plurality, as shown) of recesses 182 which define structural barrier portions 188 of lower surface 180. It is to be noted that any suitable number of recesses 182 may be provided, e.g., between 1 and 10 recesses. For some applications, recesses 182 are provided circumferentially with respect to lower surface 180 of spool 246.

Typically, spool 246 comprises a locking mechanism 145. For some applications, locking mechanism 145 is coupled, e.g., welded, at least in part to a lower surface of spool housing 248. Typically, locking mechanism 145 defines a mechanical element having a planar surface that defines slits 58. The surface of locking mechanism 145 may also be curved, and not planar. Locking mechanism 145 is shaped to provide a protrusion 156 which projects out of a plane defined by the planar surface of the mechanical element. The slits define a depressible portion 128 of locking mechanism 145 that is disposed in communication with and extends toward protrusion 156.

In a resting state of locking mechanism 145 (i.e., a locked state of spool 246), protrusion 156 is disposed within a recess 182 of spool 246. Additionally, in the locked state of spool 246, protrusion 156 is disposed within the recess of housing 248.

Depressible portion 128 is aligned with the opening at lower surface 180 of spool 246 and is moveable in response to a force applied thereto by a distal force applicator 88 that extends in a distal direction from a distal portion of longitudinal guide member 86. That is, distal force applicator 88 is configured to be disposed within the channel of spool 246. A distal end of applicator 88 is configured to push on depressible portion 128 in order to move depressible portion 128 downward so as to disengage protrusion 156 from within a recess 182 of spool and to unlock spool 246 from locking mechanism 145.

It is to be noted that the planar, mechanical element of locking mechanism 145 is shown by way of illustration and not limitation and that any suitable mechanical element having or lacking a planar surface but shaped to define at least one protrusion may be used together with locking mechanism 145.

A cap 1044 is provided that is shaped so as to define a planar surface and an annular wall having an upper surface 244 that is coupled to, e.g., welded to, lower surface 176 of spool housing 248. The annular wall of cap 1044 is shaped so as to define a recessed portion 1144 of cap 1044 that is in alignment with the recessed portion of spool housing 248. Locking mechanism 145 is disposed between lower surface 180 of spool 246 and the planar surface of cap 1044.

In an unlocked state of adjusting mechanism 240, protrusion 156 of locking mechanism 145 is disposed within recessed portion 1144 of cap 1044. In the unlocked state, force applicator 88 extends through spool 246 and pushes against depressible portion 128 of locking mechanism 145. The depressible portion is thus pressed downward, freeing protrusion 156 from within a recess 182 defined by structural barrier portions 188 of the lower portion of spool 246. Additionally, protrusion 156 is freed from within the recessed portion of spool housing 248. As a result, contracting mechanism 240 is unlocked, and spool 246 may be rotated with respect to spool housing 248.

Cap 1044 functions to restrict distal pushing of depressible portion 128 beyond a desired distance so as to inhibit deformation of locking mechanism 145. For applications in which adjusting mechanism 240 is implanted in heart tissue, cap 1044 also provides an interface between adjusting mechanism 240 and the heart tissue. This prevents interference of heart tissue on adjusting mechanism 240 during the locking and unlocking thereof. Additionally, cap 1044 prevents damage to heart tissue by depressible portion 128 as it is pushed downward.

Spool 246 is shaped so as to define a rotation-facilitating head 170. A rotation tool (not shown) is configured to slide distally along guide member 86 to engage head 170 of spool 246. The rotation tool is configured to rotate spool 246 by applying rotational force to head 170. A friction-reducing ring 172 is disposed between upper surface 178 of spool 246 and the inner surface of upper surface 160 of spool housing 248.

For some applications, as described herein, guide member 86 is not coupled to spool 246. For such applications the rotation tool used to rotate spool 246 may be shaped to provide a distal force applicator (similar to distal force applicator 88) configured to unlock spool 246 from locking mechanism 145. In the unlocked state, spool 246 may be bidirectionally rotated.

Following rotation of spool 246 such that tension member 60 is pulled sufficiently to adjust the degree of tension of member 60 so as treat tissue of the ventricle as described herein, spool 246 is then locked in place so as to restrict rotation of spool 246. Force applicator 88 is removed from within the channel of spool 246, and thereby, depressible portion 128 returns to its resting state. As depressible portion 128 returns to its resting state, protrusion 156 is introduced within one of the plurality of recesses 182 of lower surface 180 of spool 246 and within the recess of housing 248, and thereby restricts rotation of spool 246.

Spool 246 is shaped so as to provide a hole 242 or other coupling mechanism for coupling a first portion of flexible longitudinal tension member 60 to spool 246, and thereby to adjusting mechanism 240.

FIG. 5 is a schematic illustration of a system 220 comprising an implant structure 222 which comprises an adjustable annuloplasty ring structure that is coupled to two or more flexible-longitudinal-tension-member-adjusting-mechanisms 240a and 240b, as described hereinabove with reference to FIG. 1, in accordance with some applications of the present invention. For some applications, as shown, the annuloplasty ring structure comprises a partial annuloplasty ring. Adjusting mechanisms 240a and 240b typically comprise rotatable structures (e.g., spools, as described hereinbelow) which are coupled to respective first portions of flexible longitudinal tension members 60a and 60b. When system, 220 is implanted in the heart of the patient, implant structure 222 is configured to be implanted at an annulus of a native valve of a patient (e.g., an atrioventricular valve such as the mitral valve or the tricuspid valve). Tension members 60a and 60b are configured to extend toward the ventricle of the heart of the patient by passing between the leaflets of the valve or by passing through tissue of the annulus or commissures of the valve. Respective second end portions of tension members 60a and 60b are configured to be coupled to respective portions of cardiac tissue which are in the vicinity of the ventricle of the heart (e.g., portions of papillary muscle, portions of tissue at the base of the papillary muscle, portions of tissue in a vicinity of the apex, portions of tissue of an inner wall of the ventricle, and/or portions of tissue of an outer wall of the ventricle).

Rotation of the rotatable structures of mechanisms 240a and 240b in a first rotational direction pulls tight (e.g., shortens) the respective tension members 60a and 60b in order to draw the portions of cardiac tissue toward implant structure 222 (i.e., to reduce the distance between each mechanism 240 and the second end portion of the respective tension member 60). Mechanisms 240a and 240b thereby act as perimeter-adjusting mechanisms. For some applications of the present invention, system 220 functions to repair and/or effect remodeling of the portions of cardiac tissue, remodeling of the papillary muscles, and/or remodeling of a heart wall of the ventricle to treat distension. For some applications, tension members function as artificial chordae tendineae.

Flexible-longitudinal-tension-member-adjusting-mechanisms 240a and 240b, tension members 60a and 60b, contracting member 30, and flexible-longitudinal-contracting-member-adjusting-mechanism 40 shown in FIG. 4 are identical to those described hereinabove with reference to FIG. 1. For some applications, adjusting mechanisms 240a and 240b are coupled to the outer surface of body portion 224 of structure 222 by rings 241, as described hereinabove with reference to FIGS. 2A-B. The annuloplasty structure of implant structure 221 comprises a body portion 224 which is similar to body portion 24 described hereinabove with reference to FIG. 1. It is to be noted that although body portion 224 is shown as comprising only coiled portion 12, body portion 224 may comprise a braided mesh or may be surrounded by a braided mesh, as described hereinabove with reference to FIG. 1.

Adjusting mechanism 40 is coupled to a first end 221 of body portion 224. Flexible contracting member 30 is coupled at a first end portion thereof to adjusting mechanism 40. A second end portion of flexible contracting member 30 is coupled to a second end 223 of body portion 224. Typically, during the resting state, flexible contracting member 30 is disposed in parallel with the longitudinal axis of structure 222. That is, flexible member 30, for some applications does not comprise a continuous band that runs through the entire lumen of the annuloplasty devices described herein, and flexible member 30 has at least one free end portion.

Typically, first end 221 of body portion 224 is welded to coupling member 31 of a housing 344 surrounding spool 46. Housing 344 is similar to housing 44 described herein, with the exception that coupling member 35 of housing 44 is replaced with a first suture fastener 41. First suture fastener 41 is shaped to define a hole 43 for passage therethrough of a suture to suture structure 222 to tissue of the patient. Second end 223 of body portion 224 comprises a second suture fastener 37 that is shaped to define a hole 47 for passage therethrough of a suture.

Reference is now made to FIGS. 1-3 and 5. As shown in FIG. 3, spool 46 is shaped so as to provide one or more holes 42a and 42b or other coupling mechanism for coupling a first portion of flexible longitudinal contracting member 30 to spool 46, and thereby to adjusting mechanism 40. In response to a rotational force applied to spool 46 in a first rotational direction, successive portions of flexible contracting member 30 are wrapped around spool 46 in order to tighten contracting member 30. That is, during rotation of spool 46 in the first direction, successive portions of member 30 contact spool 46. As flexible contracting member 30 is wrapped around spool 46, the second end portion of member 30 is pulled toward adjusting mechanism 40. Pulling the second end of flexible contracting member 30 toward mechanism 40 pulls the respective second ends 23 of structures 122 and 222 toward the respective first ends 21 of structures 122 and 222. Responsively, the compressible element of body portion 24 is longitudinally compressed, thereby contracting structures 122 and 222.

It is to be noted that the contraction of structures 122 and 222 is reversible. That is, rotating spool 46 in a second rotational direction that opposes the first rotational direction used to contract the annuloplasty structure, unwinds a portion of flexible contracting member 30 from around spool 46. Unwinding the portion of flexible contracting member 30 from around spool 46 thus feeds the portion of flexible contracting member 30 back into the lumen of body portion 24 of respective structures 122 and 222, thereby slackening the remaining portion of flexible contracting member 30 that is disposed within the lumen of body portion 24. Responsively, the annuloplasty structure gradually relaxes and expands (i.e., with respect to its contracted state prior to the unwinding) as the compressible element of body portion 24 gradually expands.

Figure 6A:
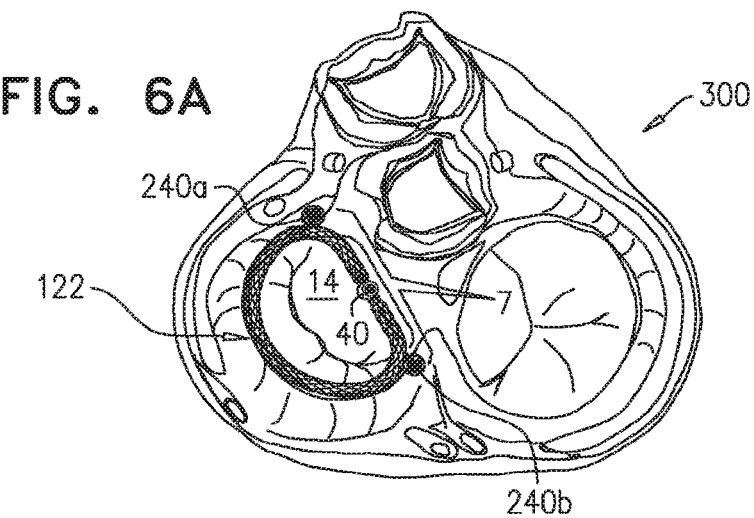
FIGS. 6A-B, 7A-B, and 8A-B are schematic illustrations of placing the implant structure of FIG. 1 in a heart of a patient, in accordance with some applications of the present invention.
Figure 6B:
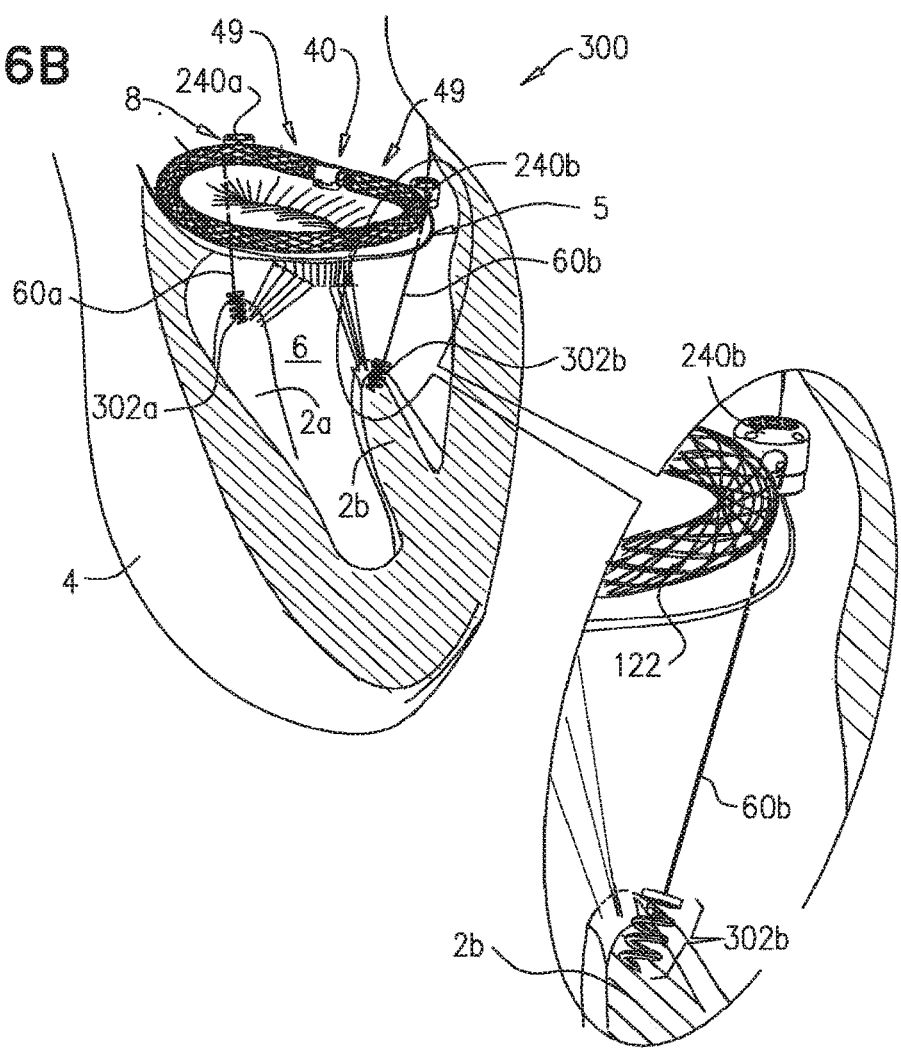

Reference is now made to FIGS. 6A-B, which are schematic illustrations of a system 300 for repairing a mitral valve 14 and papillary muscles 2a and 2b of a heart 4 of the patient using implant structure 122, as described hereinabove with reference to FIG. 1, in accordance with some applications of the present invention. Implant structure 122 is positioned along the annulus of valve 14 and is coupled thereto using sutures, anchors, and/or any other suitable tissue-coupling element. As shown, implant 122 is positioned along the annulus in a manner in which portions 49 and mechanism 40 are disposed along the annulus at an anterior section 7 of valve 14, adjusting mechanism 240a is implanted in a vicinity of a left fibrous trigone 8 of valve 14, and adjusting mechanism 240b is implanted in a vicinity of a right fibrous trigone 5 of valve 14. Following the coupling of structure 122 to the annulus of valve 14, tension members 60a and 60b are pulled down into a ventricle 6 of heart 4 by the operating physician (e.g., using his/her hands or using a tool). For some applications, members 60a and 60b pass through an opening created in the annulus of valve 14 (e.g., by puncturing a needle therethrough). Alternatively, members 60a and 60b pass between the leaflets of valve 14. Further alternatively, members 60a and 60b pass through respective commissures of valve 14.

Respective tissue-coupling elements 302a and 302b are coupled to respective distal portions of members 60a and 60b, respectively. Elements 302a and 302b comprise helical tissue anchors by way of illustration and not limitation. That is, elements 302a and 302b may comprise any suitable tissue-engaging structure. As shown, elements 302a and 302b are configured to be coupled to tissue of respective papillary muscles 2a and 2b.

Following the coupling of structure 122 to the annulus of valve 14 and/or the coupling of tissue-engaging elements 302a and 302b, the spool of adjusting mechanism 40 is rotated in order to adjust a dimension of the annuloplasty structure of implant structure 122 and thereby to adjust a dimension of the annulus and relative positioning of the leaflets of valve 14. For example, in response to rotation of the spool of mechanism 40 in a first rotational direction thereof, the annuloplasty structure is contracted in order to contract the annulus and to draw together the leaflets of valve 14.

Following the coupling of tissue-engaging elements 302a and 302b, the spools of adjusting mechanisms 240a and 240b are rotated in order to adjust a degree of tension of tension members 60a and 60b. For example, in response to rotation of the spools of mechanisms 240a and 240b in a first rotational direction thereof, tension members 60a and 60b are pulled tight in order to pull on papillary muscles 2a and 2b.

For such applications, members 60a and 60b function to relocate and/or alter a geometry and/or spatial configuration of papillary muscles 60a and 60b. For some applications, members 60a and 60b function as artificial chordae tendineae.

For some applications, members 60a and 60b function to repair a distension of the heart wall surrounding ventricle 6.

It is to be noted that implant structure 122 and tension members 60a and 60b may be implanted using an open-heart or minimally-invasive procedure.

For some applications, whether the implant structure and tension members are implanted using an open-heart or a minimally-invasive procedure, adjustment (e.g., rotation) of mechanisms 40, 240a, and 240b is performed off-pump (e.g., while the heart is beating), using a tool to facilitate the rotation of the adjusting mechanisms (e.g., elongate tool 50, force applicator 88, or similar). For example, following an open-heart procedure, heart tissue may be closed so as to provide only a small channel through which the tool extends, such that the heart can beat without leaking. Adjustment (e.g., rotation) of the adjusting mechanisms off-pump facilitates adjustment of the valve annulus and ventricle, while monitoring heart function and/or blood flow using imaging techniques, e.g., such that the physician may adjust until optimal heart function and/or blood flow is attained. For example, the physician may advance the tool (e.g., facilitated by imaging, such as fluoroscopy and/or ultrasound), and then sequentially, and/or repeatedly adjust (e.g., rotate) mechanism 40, mechanism 240*a*, and mechanism 240*b* (e.g., facilitated by imaging, such as Doppler ultrasound, in real-time and/or between adjustments). The order in which the adjusting mechanisms are adjusted may be decided by the physician, such as in response to the blood flow monitoring.

Figure 7A:
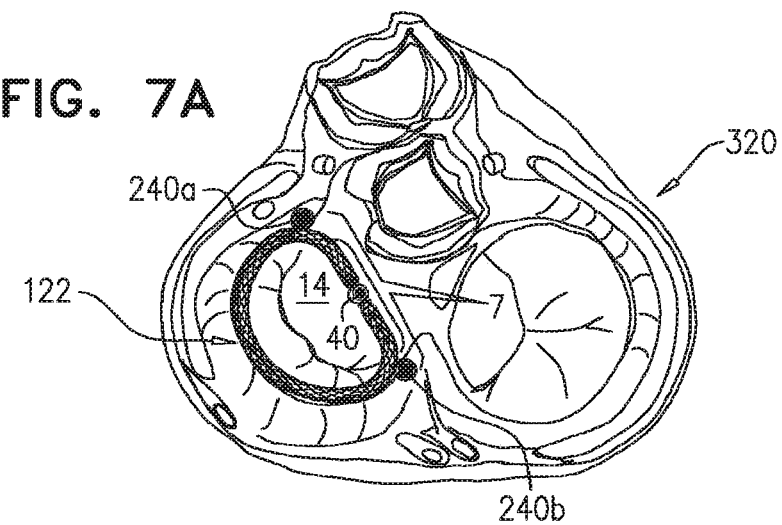
Figure 7B:
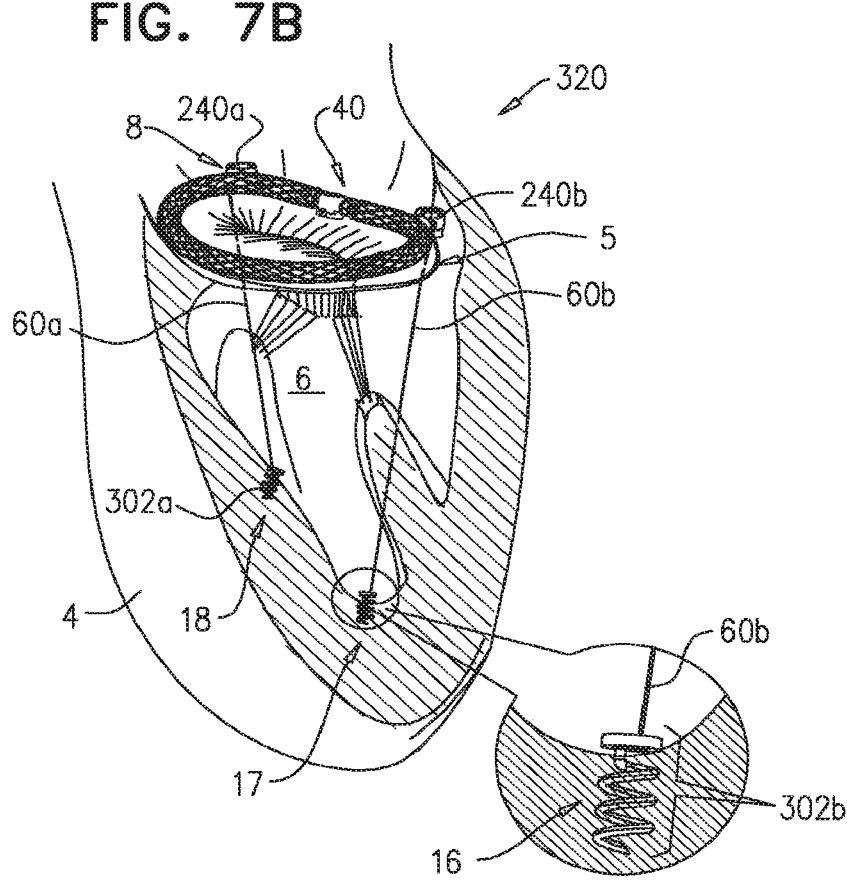

Reference is now made to FIGS. 7A-B, which are schematic illustrations of a system 320 for repairing a mitral valve 14 and portions of tissue of ventricle 6 of a heart 4 of the patient, as described hereinabove with reference to FIGS. 6A-B, with the exception that tissue-engaging elements 302*a* and 302*b* are coupled to respective portions of tissue along an inner wall of ventricle 6, in accordance with some applications of the present invention. As shown, tissue-engaging element 302*a* is coupled to a portion 16 of tissue in a vicinity of an apex 17 of heart 4, and tissue-engaging element 302*b* is coupled to a portion 18 of tissue at a base of the papillary muscle.

For some applications, members 60*a* and 60*b* function to relocate and/or alter a geometry and/or spatial configuration of papillary muscles 60*a* and 60*b*. For other applications, members 60*a* and 60*b* function to repair a distension of the heart wall surrounding ventricle 6. For yet other applications, members 60*a* and 60*b* function as artificial chordae tendineae.

Figure 8A:
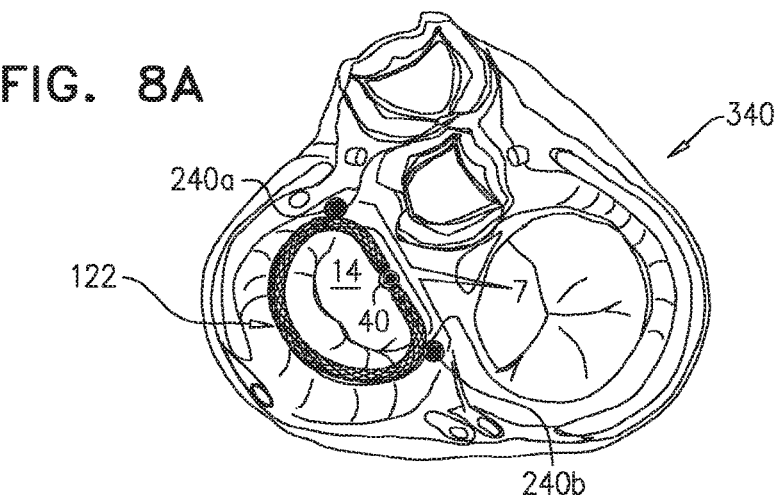
Figure 8B:
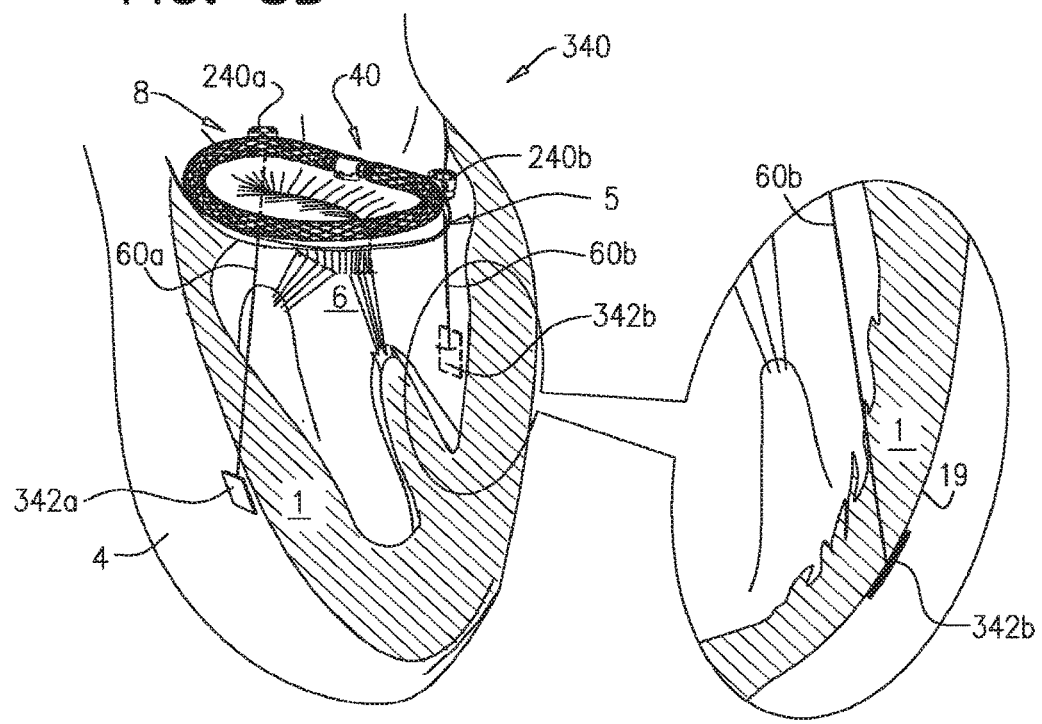

Reference is now made to FIGS. 8A-B, which are schematic illustrations of a system 340 for repairing a mitral valve 14 and portions of tissue of ventricle 6 of a heart 4 of the patient, as described hereinabove with reference to FIGS. 6A-B and 7A-B, with the exception that respective second portions of tension members 60*a* and 60*b* are configured to extend trans-myocardially to an external surface 19 of heart 4, in accordance with some applications of the present invention.

A respective tissue-engaging element is coupled to the second portion of each tension member 60*a* and 60*b*. Each tissue-engaging element comprises a respective tissue-abutting pad 342*a* and 342*b* configured to rest against respective portions of surface 19 of heart 4.

For such applications, members 60*a* and 60*b* function to repair a distension of the heart wall surrounding ventricle 6. For some applications, members 60*a* and 60*b* function to relocate and/or alter a geometry and/or spatial configuration of papillary muscles 60*a* and 60*b*.

Reference is now made to FIGS. 9A-B, which are schematic illustrations of an implant structure 400 comprising an annuloplasty ring structure as described hereinabove with reference to FIG. 1, with the exception that structure 400 comprises a proximity-adjusting-mechanism 420, in accordance with some applications of the present invention. Structure 400 defines an anterior-configured portion 402 configured for placement adjacent the anterior leaflet of the mitral valve. Additionally, structure 400 defines a posterior-configured portion 404 configured for placement adjacent the posterior leaflet of the mitral valve. For some applications, portion 402 is flexible and less longitudinally compressible than portion 404. For example, portion 402 may comprise portions 49 described hereinabove with reference to FIG. 1.

As described hereinabove, adjusting mechanism 40 is configured to adjust a dimension of structure 400 by contracting and expanding a contracting member disposed within the lumen of body portion 24.

As shown, flexible-longitudinal-contracting-member-adjusting-mechanism 40 is aligned with body portion 24 along the longitudinal axis thereof, as described hereinabove with reference to FIG. 1. Proximity-adjusting-mechanism 420 comprises any rotatable adjusting mechanism described herein (e.g., as described hereinabove with reference to FIGS. 3 and 4). Mechanism 420 comprises a housing 426 configured to surround a portion of the outer surface of body portion 24, typically surrounding a portion of body portion 24 that opposes adjusting mechanism 40. The rotatable structure of proximity-adjusting mechanism 420 is coupled to a first portion of a flexible elongate member 422. A second portion 424 of elongate member 422 is coupled to housing 44 (e.g., typically at an external surface thereof).

Typically, the rotatable structure of adjusting mechanism 420 comprises a spool. In response to rotation of the rotatable structure of adjusting mechanism 420 in a first rotational direction, successive portions of elongate member 422 are wound around the spool and pull tight the portion of elongate member 422 disposed between adjusting mechanisms 40 and 420. In response, a portion of posterior-configured portion 404 is pulled in the direction as indicated by the arrow in FIG. 9B. Thus, adjusting mechanism 420 is configured to adjust a septo-lateral dimension of structure 400 and of the annulus of the mitral valve when structure 400 is implanted at the annulus of the mitral valve in order to adjust the distance between the leaflets of the valve and to adjust opposing portions of the annulus of the mitral valve.

It is to be noted that the rotation of the rotational structure of adjusting mechanism 420 is reversible, and that following rotation of the rotatable structure in order to pull structure 400 into the configuration shown in FIG. 9B, the rotatable structure may be rotated in a second rotational direction that opposes the first rotational direction in order for structure 400 to assume the configuration shown in FIG. 9A.

It is to be noted that mechanisms 40 and 420 may be positioned at any suitable location along body portion 24 of structure 400.

As shown, the annuloplasty structure of implant structure 400 defines a substantially ring-shaped configuration, e.g., a "D"-shaped configuration, as shown, which conforms to the shape of the annulus of a mitral valve of the subject. For applications in which structure 400 is implanted at a tricuspid valve of the patient, the annuloplasty structure assumes a shape suitable to fit the tricuspid valve (e.g., a substantially oval shape).

It is to be noted that structure 400 is shown independently of flexible-longitudinal-tension-member-adjusting-mechanisms 240 and tension members 60 by way of illustration and not limitation. For some applications, structure 400 is coupled to one or more mechanisms 240.

Figure 10A:
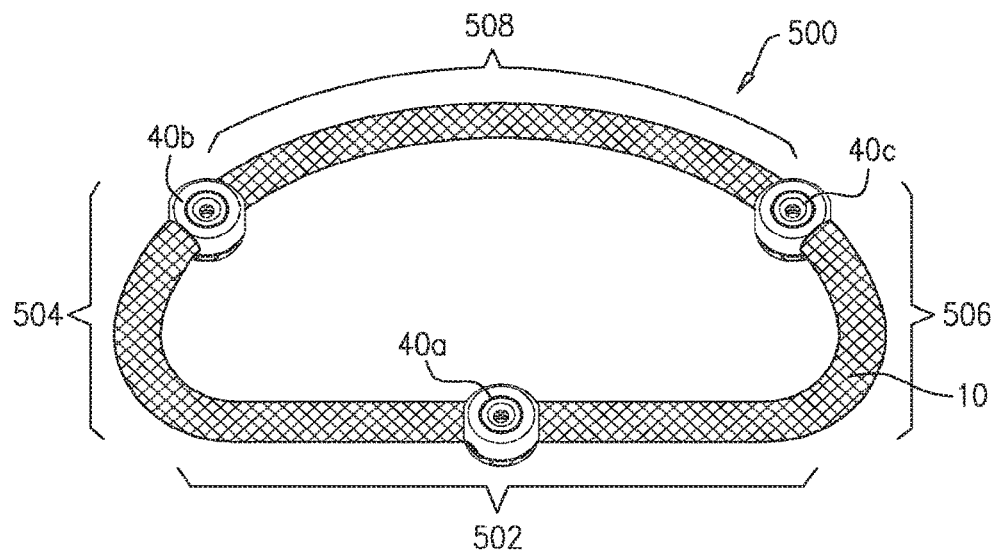
FIGS. 10A-B are schematic illustrations an implant structure comprising a plurality of adjusting mechanisms which shape the structure into a saddle-shaped ring, in accordance with some applications of the present invention.
Figure 10B:
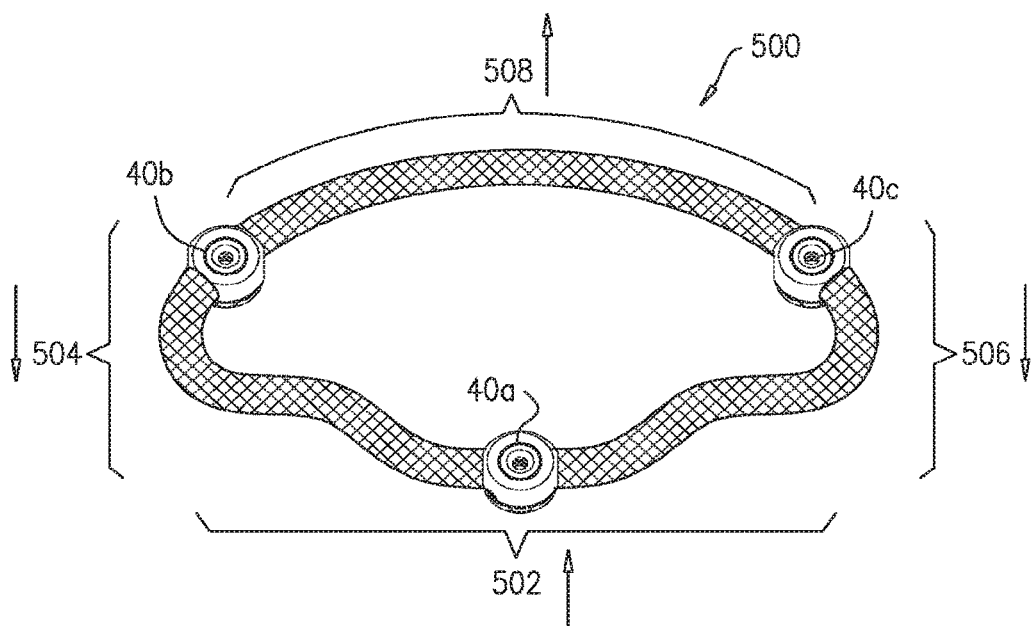

Reference is now made to FIGS. 10A-B, which are schematic illustrations of an implant structure 500 comprising an annuloplasty ring structure configured to transition between a substantially planar configuration (FIG. 10A) and a saddle-shaped configuration (FIG. 10B) in response to rotation of two or more (e.g., three, as shown) flexible-longitudinal-contracting-member-adjusting-mechanisms 40. As shown, structure 500 comprises three adjusting mechanisms 40a, 40b, and 40c that are aligned with the body portion of structure 500 along a longitudinal axis thereof, as described hereinabove with reference to FIG. 1. Adjusting mechanisms 40a, 40b, and 40c are described hereinabove with reference to FIGS. 1 and 3. It is to be noted, however, that the adjusting mechanisms may comprise adjusting mechanisms 240, as described hereinabove with reference to FIGS. 1 and 4.

Structure 500 defines an anterior-configured portion 502, a posterior-configured portion 508, and first and second commissural portions 504 and 506, respectively. Typically, one or more flexible longitudinal contracting members (e.g., contracting member 30, as described herein) is disposed within the lumen of the body portion of structure 500. For some applications the number of contracting members disposed within the lumen of structure 500 corresponds to the number of adjusting mechanisms 40 coupled to structure 500.

In response to rotation of the rotatable structures of adjusting mechanisms 40a, 40b, and 40c in first rotational directions, the one or more contracting members are pulled tight (e.g., in response to winding successive portions of the one or more contracting members around the respective rotational structures of adjusting mechanisms 40a, 40b, and 40c). Responsively, anterior-configured portion 502 and posterior-configured portion 508 are pulled upward, and first and second commissural portions 504 and 506 are pulled downward, in the direction as indicated by the arrows, such that structure 500 assumes a saddle-shape (as shown in FIG. 10B).

It is to be noted that the rotation of the rotational structure of adjusting mechanisms 40a, 40b, and 40c is reversible, and that following rotation of the rotatable structure in order to pull structure 500 into the configuration shown in FIG. 10B, the rotatable structure may be rotated in a second rotational direction that opposes the first rotational direction in order for structure 500 to assume the configuration shown in FIG. 10A.

As shown, the annuloplasty structure of implant structure 500 defines a substantially ring-shaped configuration, e.g., a "D"-shaped configuration, as shown, which conforms to the shape of the annulus of a mitral valve of the subject. For applications in which structure 500 is implanted at a tricuspid valve of the patient, the annuloplasty structure assumes a shape suitable to fit the tricuspid valve (e.g., a substantially oval shape).

It is to be noted that structure 500 is shown independently of flexible-longitudinal-tension-member-adjusting-mechanisms 240 and tension members 60 by way of illustration and not limitation. For some applications, structure 500 is coupled to one or more mechanisms 240.

It is to be noted that mechanisms 40 may be positioned at any suitable location along body portion 24 of structure 500. It is to be further noted that any suitable number of mechanisms 40 may be coupled to structure 500.

Reference is made to FIG. 11. Following implantation of the implant structures described herein, the implant structures may be adjusted while the patient is not on a cardiopulmonary bypass pump (i.e., "off pump", e.g., while the heart of the patient is beating) (e.g., as described hereinabove with reference to FIGS. 6A-B). Adjustment (e.g., rotation) of the adjusting mechanisms off-pump facilitates adjustment while monitoring heart and/or valve function, and/or blood flow using imaging techniques, such as fluoroscopy and ultrasound (e.g., Doppler ultrasound), such that an operating physician 520 may adjust until optimal heart function and/or blood flow is attained. For example, and as shown in FIG. 11, two or more elongate rotation tools 522 (e.g., elongate rotation tools 522a, 522b, and 522c), configured to adjust rotate spool 46 and/or spool 246, may extend from outside of the body of the patient 524, to respective adjusting mechanisms of the implant structure 524, such that operating physician 520 can adjust the adjusting mechanisms of the annuloplasty structure while monitoring a display 526 that displays information indicative of the heart and/or valve function and/or the blood flow.

The order in which the adjusting mechanisms are adjusted may be decided by the physician, such as in response to the blood flow monitoring. For example, the operating physician may adjust adjusting mechanism 40, then observe display 526, then adjust one or more adjusting mechanisms 240. Alternatively, the physician may adjust one or more adjusting mechanisms 240 first, and subsequently adjust adjusting mechanism 40. It will be understood by those familiar with the art, that any order of adjustment is possible, and similarly, that display 526 may be monitored simultaneously with the adjustments, and/or between adjustments. It is to be noted that the scope of the invention includes other feedback systems, such as audio and/or tactile feedback, in addition to, or instead of, display 526.

Reference is now made to FIGS. 1, 2B, 5, 6A-B, 7A-B, 8A-B, and 9A-B. It is to be noted that the annuloplasty structures described herein may be shaped so as to define a saddle-shaped ring.

Reference is now made to FIGS. 1, 2B, 5, 6A-B, 7A-B, 8A-B, 9A-B, and 10A-B. It is to be noted that for any implant structure described herein, adjusting mechanism 240 may be used in place of adjusting mechanism 40, and adjusting mechanism 40 may be used in place of adjusting mechanism 240, mutatis mutandis. As described hereinabove, adjusting mechanisms 40 and 240 are rotatable in first and second opposing rotational directions (i.e., are bidirectionally rotatable), and are thereby configured to reversibly (1) tighten and loosen (e.g., shorten and lengthen) flexible contracting member 30, and thereby reversibly expand and contract the annuloplasty structure, and (2) tighten and loosen tension member 60, and thereby reversibly reshape tissue of the ventricle. It is to be further noted that adjusting mechanisms 240 described herein may be provided together with or independently of guide members 86.

Reference is again made to FIGS. 1, 2B, 5, 6A-B, 7A-B, 8A-B, 9A-B, and 10A-B. It is to be noted that any suitable number of flexible-longitudinal-tension-member-adjusting-mechanisms 240 may be coupled to the annuloplasty structures of implant structures 122, 222, 400 and 500. For some applications, only one flexible-longitudinal-tension-member-adjusting-mechanism 240 is coupled to the annuloplasty structures of implant structures 122, 222, 400, and 500. It is to be further noted that any suitable number of flexible longitudinal tension members 60 may be coupled to each flexible-longitudinal-tension-member-adjusting-mechanism 240.

Reference is now made to FIGS. 1, 2B, 5, 6A-B, 7A-B, 8A-B, 9A-B, and 10A-B. It is to be noted that although systems 300, 320, and 340 show implant structure 122, it is to be noted that the scope of the present invention includes the implantation of implant structure 222, as described hereinabove with reference to FIG. 5, implant structure 400, as described hereinabove with reference to FIGS. 9A-B, or implant structure 500, as described hereinabove with reference to FIGS. 10A-B. Additionally, it is to be noted that adjusting mechanisms 240a and 240b are shown as being disposed in the vicinities of respective fibrous trigones 8 and 10 by way of illustration and not limitation, and that mechanisms 240a and 240b may be positioned at anywhere along the body portion of the annuloplasty structure of implant structure 122. For example, mechanisms 240a and 240b may be sutured to the body portion prior to delivery of structure 122. Alternatively, mechanisms 240a and 240b are coupled to respective rings 241 (as described hereinabove with reference to FIGS. 2A-B), and mechanisms 240a and 240b are slid to desired locations along the body portion of the annuloplasty structure. It is to be further noted that housing 44 (and mechanism 40) may be disposed at any suitable location along structure 122, and not only in the portion of structure 122 configured to be disposed at the anterior section 7 of valve 14.

It is to be noted that systems 120, 220, 300, 320, 340, and structures 400 and 500 for repairing a dilated annulus of the subject may be used to repair any cardiac valve of the subject, e.g., the mitral valve, the tricuspid valve, the aortic valve, and the pulmonary valve. It is to be still further noted that systems described herein for treatment of valves may be used to treat other annular muscles within the body of the patient. For example, the systems described herein may be used in order to treat a sphincter muscle within a stomach of the subject.

Typically, the annuloplasty ring structures described herein, the adjusting mechanisms, and the flexible longitudinal members are advanced and implanted in an open-heart procedure. For some applications, devices described herein may be implanted using a minimally-invasive or percutaneous transcatheter procedure.

Additionally, the scope of the present invention includes applications described in one or more of the following:

U.S. patent application Ser. No. 12/435,291 to Maisano et al., entitled, "Adjustable repair chords and spool mechanism therefor," filed on May 4, 2009, which published as US Patent Application Publication 2010/0161041, and which issued as U.S. Pat. No. 8,147,542;

U.S. patent application Ser. No. 12/437,103 to Zipory et al., entitled, "Annuloplasty ring with intra-ring anchoring," filed on May 7, 2009, which published as US Patent Application Publication 2010/0286767, and which issued as U.S. Pat. No. 8,715,342;

U.S. patent application Ser. No. 12/548,991 to Maisano et al., entitled, "Implantation of repair chords in the heart," filed on Aug. 27, 2009, which published as US Patent Application Publication 2010/0161042, and which issued as U.S. Pat. No. 8,808,368;

PCT Patent Application PCT/IL2009/001209 to Cabiri et al., entitled, "Adjustable annuloplasty devices and mechanisms therefor," filed on Dec. 22, 2009, which published as PCT Publication WO 10/073246;

PCT Patent Application PCT/IL2010/000357 to Maisano et al., entitled, "Implantation of repair chords in the heart," filed on May 4, 2010, which published as WO 10/128502; and/or PCT Patent Application PCT/IL2010/000358 to Zipory et al., entitled, "Deployment techniques for annuloplasty ring and over-wire rotation tool," filed on May 4, 2010, which published as WO 10/128503.

All of these applications are incorporated herein by reference. Techniques described herein can be practiced in combination with techniques described in one or more of these applications.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use with an implant structure, a first tool, a second tool, and a longitudinal guide member, the implant structure including (i) a body portion, (ii) a first implant-adjustment mechanism coupled to the body portion and configured to adjust the implant structure, and (iii) a second implant-adjustment mechanism coupled to the body portion, the method comprising:

delivering the implant structure to a heart of a subject while the first implant-adjustment mechanism is coupled to the first tool, and the second implant-adjustment mechanism is coupled to the longitudinal guide member;

subsequently, coupling the implant structure to tissue of the heart; and subsequently, advancing the second tool along the longitudinal guide member to the second implant-adjustment mechanism, the second tool configured to actuate the second implant-adjustment mechanism.

2. The method according to claim 1, wherein delivering the implant structure to the heart comprises delivering the implant structure to the heart using the first tool.

3. The method according to claim 1, wherein coupling the implant structure to the tissue comprises suturing the implant structure to the tissue.

4. The method according to claim 1, further comprising, subsequently to coupling the implant structure to the tissue, adjusting a first dimension of the implant structure using the first tool, and adjusting a second dimension of the implant structure using the second tool.

5. The method according to claim 4, wherein the first implant-adjustment mechanism includes a first spool, and wherein adjusting the first dimension comprises adjusting the first dimension by rotating the first spool using the first tool.

6. The method according to claim 5, wherein the second implant-adjustment mechanism includes a second spool, and wherein adjusting the second dimension comprises adjusting the second dimension by rotating the second spool using the second tool.

7. The method according to claim 1, wherein the body portion includes an annuloplasty structure that is coupled to the first adjustment mechanism and to the second adjustment mechanism, and wherein coupling the body portion to the tissue comprises coupling the annuloplasty structure to a valve annulus of the heart.

8. The method according to claim 7, wherein delivering the implant structure to the heart comprises delivering the implant structure to the heart while the annuloplasty structure is coupled to an annuloplasty sizer.

9. The method according to claim 8, further comprising, prior to delivering the implant structure, contracting the annuloplasty structure around the sizer using the first tool.

10. The method according to claim 7, wherein:
the annuloplasty structure has a perimeter, and
the method further comprises, subsequently to coupling the annuloplasty structure to the valve annulus, contracting the perimeter by adjusting the first implant-adjustment mechanism using the first tool.

11. The method according to claim 10, further comprising, subsequently to coupling the annuloplasty structure to the valve annulus, adjusting the second implant-adjustment mechanism using the second tool.

12. The method according to claim 11, wherein the implant structure further includes a flexible longitudinal tension member, a first end portion of the tension member being coupled to the second adjustment mechanism, and wherein coupling the implant structure to the tissue further comprises coupling a second end portion of the tension member to tissue of a ventricle of the heart.

13. The method according to claim 12, wherein coupling the second end portion of the tension member to the tissue of the ventricle comprises coupling the second end portion of the tension member to a papillary muscle of the heart.

14. The method according to claim 12, wherein the implant structure includes a tissue anchor coupled to the second end portion of the tension member, and wherein coupling the second end portion of the tension member to the tissue of the ventricle comprises anchoring the second end portion of the tension member to the tissue of the ventricle using the tissue anchor.

15. The method according to claim 12, wherein adjusting the second adjustment mechanism comprises, subsequently to coupling the second end portion of the tension member to the tissue of the ventricle, drawing the tissue of the ventricle toward the annuloplasty structure by tensioning the tension member by adjusting the second adjustment mechanism.

16. The method according to claim 1, further comprising:
subsequently to coupling the implant to the tissue, actuating the first implant-adjustment mechanism using the first tool, and
subsequently to advancing the second tool along the longitudinal guide member to the second implant-adjustment mechanism, actuating the second implant-adjustment mechanism using the second tool.

17. A method for use with an implant structure, a first tool, a second tool, and a longitudinal guide member, the implant structure including (i) an annuloplasty structure, (ii) a first implant-adjustment mechanism coupled to the annuloplasty structure, and (iii) a second implant-adjustment mechanism coupled to the annuloplasty structure, the method comprising:
delivering the implant structure to a heart of a subject while the first tool is coupled to the first adjustment mechanism, and the longitudinal guide member is coupled to the second adjustment mechanism;
subsequently, coupling the annuloplasty structure to a valve annulus of the heart such that the annuloplasty structure has a perimeter; and
subsequently:
contracting the perimeter by adjusting the first adjustment mechanism using the first tool;
advancing the second tool along the longitudinal guide member to the second adjustment mechanism; and
adjusting the second adjustment mechanism using the second tool.

18. The method according to claim 17, wherein the implant structure further includes a flexible longitudinal tension member, a first end portion of the tension member being coupled to the second adjustment mechanism, and wherein coupling the implant structure to the tissue further comprises coupling a second end portion of the tension member to tissue of a ventricle of the heart.

19. The method according to claim 18, wherein coupling the second end portion of the tension member to the tissue of the ventricle comprises coupling the second end portion of the tension member to a papillary muscle of the heart.

20. The method according to claim 18, wherein the implant structure includes a tissue anchor coupled to the second end portion of the tension member, and wherein coupling the second end portion of the tension member to the tissue of the ventricle comprises anchoring the second end portion of the tension member to the tissue of the ventricle using the tissue anchor.

21. The method according to claim 18, wherein adjusting the second adjustment mechanism comprises, subsequently to coupling the second end portion of the tension member to the tissue of the ventricle, drawing the tissue of the ventricle toward the annuloplasty structure by tensioning the tension member by adjusting the second adjustment mechanism.

22. A method for use with an implant structure, a first tool, a second tool, and a longitudinal guide member, the method comprising:
delivering the implant structure to a heart of a subject, the implant structure including:
(i) a first adjustment mechanism to which the first tool is coupled, and
(ii) a second adjustment mechanism to which the longitudinal guide member is coupled;
subsequently, coupling the implant structure to tissue of the heart;
subsequently to coupling the implant structure to the tissue, adjusting a first dimension of the implant structure using the first tool, wherein the first adjustment mechanism includes a first spool, and wherein adjusting the first dimension comprises adjusting the first dimension by rotating the first spool using the first tool;
advancing the second tool along the longitudinal guide member to the second adjustment mechanism and adjusting a second dimension of the implant structure using the second tool, wherein the second adjustment mechanism includes a second spool, and wherein adjusting the second dimension comprises adjusting the second dimension by rotating the second spool using the second tool.

* * * * *